(12) United States Patent
Lindsay et al.

(10) Patent No.: US 8,877,945 B2
(45) Date of Patent: Nov. 4, 2014

(54) REDOX DRUG DERIVATIVES

(75) Inventors: Derek Lindsay, Liverpool (GB); Peter Jackson, Liverpool (GB)

(73) Assignee: Redx Pharma Limited, Liverpool (GB)

( * ) Notice: Subject to any disclaimer, the term of this patent is extended or adjusted under 35 U.S.C. 154(b) by 158 days.

(21) Appl. No.: 13/319,377

(22) PCT Filed: May 17, 2010

(86) PCT No.: PCT/GB2010/050797
§ 371 (c)(1),
(2), (4) Date: Dec. 8, 2011

(87) PCT Pub. No.: WO2010/131054
PCT Pub. Date: Nov. 18, 2010

(65) Prior Publication Data
US 2012/0077974 A1    Mar. 29, 2012

(30) Foreign Application Priority Data

May 15, 2009  (GB) .................................. 0908338.7
Apr. 13, 2010  (GB) .................................. 1006112.5

(51) Int. Cl.
| | | |
|---|---|---|
| C07D 401/10 | (2006.01) | |
| C07D 209/48 | (2006.01) | |
| C07D 317/30 | (2006.01) | |
| C07D 405/06 | (2006.01) | |

(52) U.S. Cl.
USPC ........... 548/472; 548/479; 544/101; 544/363; 560/115; 549/452

(58) Field of Classification Search
USPC ........... 544/101, 363; 548/472, 479; 560/115; 549/452
See application file for complete search history.

(56) References Cited

U.S. PATENT DOCUMENTS

| | | | |
|---|---|---|---|
| 4,808,585 A | 2/1989 | Grohe et al. | |
| 4,965,262 A | 10/1990 | Kametaka et al. | |
| 4,971,970 A | 11/1990 | Miyamoto et al. | |
| 5,235,054 A | 8/1993 | Jefson | |
| 5,416,096 A | 5/1995 | Petersen et al. | |
| 5,457,104 A | 10/1995 | Bartel et al. | |
| 5,463,053 A | 10/1995 | Hayakawa et al. | |
| 5,480,879 A | 1/1996 | Petersen et al. | |
| 5,519,016 A | 5/1996 | Kimura et al. | |
| 5,527,910 A | 6/1996 | Kim et al. | |
| 5,648,379 A | 7/1997 | Von Itzstein et al. | |
| 5,654,318 A | 8/1997 | Takemura et al. | |
| 5,665,754 A | 9/1997 | Feldman et al. | |
| 5,703,081 A | 12/1997 | Miyake et al. | |
| 5,739,160 A | 4/1998 | Mittendorf et al. | |
| 5,763,483 A | 6/1998 | Bischofberger et al. | |
| 5,849,752 A | 12/1998 | Grunenberg et al. | |
| 5,952,375 A | 9/1999 | Bischofberger et al. | |
| 6,001,876 A * | 12/1999 | Singh .............................. 514/561 |
| 6,111,132 A | 8/2000 | Kim et al. | |
| 6,251,935 B1 | 6/2001 | Schoenen et al. | |
| 6,278,013 B1 | 8/2001 | Bartel et al. | |
| 6,340,702 B1 | 1/2002 | Honda et al. | |
| 6,562,861 B1 | 5/2003 | Babu et al. | |
| 6,680,054 B1 | 1/2004 | Reece et al. | |
| 7,176,313 B2 | 2/2007 | Takemura et al. | |
| 7,179,805 B2 | 2/2007 | Grant, III et al. | |
| 7,888,337 B2 | 2/2011 | Wong et al. | |
| 2006/0014732 A1 | 1/2006 | Hofmann | |
| 2007/0225261 A1 | 9/2007 | Miller et al. | |

FOREIGN PATENT DOCUMENTS

| | | |
|---|---|---|
| DE | 4200414 | 7/1993 |
| EP | 0539204 | 4/1993 |
| EP | 0823428 | 2/1998 |
| JP | 61189281 | 8/1986 |
| JP | 2004099494 | 4/2004 |
| WO | WO-00/25765 | 5/2000 |
| WO | WO-2009010554 A1 | 1/2009 |
| WO | WO-2009/053446 | 4/2009 |

OTHER PUBLICATIONS

International Search Report and Written Opinion mailed Oct. 8, 2012 for Singapore Patent Application No. 201108379-7 (12 pages).
Shie et al., "A Concise and Flexible Synthesis of the Potent Anti-Influenza Agents Tamiflu and Tamiphosphor," Angew. Chem. Int. Ed. vol. 47, pp. 5788-5791 (2008).
Clement, "Reduction of N-Hydroxylated Compounds: Amidoximes (N-Hydroxyamidines) as Pro-Durgs of Amidines," Drug Metabolism Reviews, vol. 34 No. 3, pp. 565-579 (2002).
Ettmayer et al., "Lessons Learned from Marketed and Investigational Prodrugs," Journal of Medicinal Chemistry, vol. 47 No. 10, May 6, 2004 (13 pages).
Ettmayer et al., "Lessons Learned from Marketed and Investigational Prodrugs," Journal of Medicinal Chemistry, vol. 47, No. 10, pp. 2393-2404 (May 6, 2004).
Clement, "Reduction of N-Hydroxylated Compounds: Amidoximes (N-Hydroxyamidines) as Pro-Drugs of Amidines," Drug metabolism Reviews, vol. 34, No. 3, pp. 565-579 (Jan. 1, 2002).

(Continued)

*Primary Examiner* — Kahsay Habte
(74) *Attorney, Agent, or Firm* — Bingham McCutchen LLP

(57) ABSTRACT

The present invention provides redox drug derivatives. In particular, 9-fluoro-2,3-dihydro-3-methyl-10-(4-methyl-1-piperazinyl)-7-oxo-7H-pyrido[1,2,3-de]-1,4-benzoxazine-6-carboxylic acid, 1-ethyl-6-fluoro-1,4-dihydro-7-(4-methyl-1-piperazinyl)-4-oxo-3-quinolinecarboxylic acid, (3R,4R,5S)-4-(acetylamino)-5-amino-3-(1-ethylpropoxy)-1-cyclohexene-1-carboxylic acid ethyl ester, (3S)-3-(aminomethyl)-5-methylhexanoic acid, (3S)-1-[2-(2,3-dihydro-5-benzofuranyl)ethyl]-α,α-diphenyl-3-pyrrolidineacetamide, (1S,2S,3S,4R)-3-[(1S)-1-acetamido-2-ethyl-butyl]-4-(diaminomethyleneamino)-2-hydroxy-cyclopentane-1-carboxylic acid and (2R,3R,4S)-4-[(diaminomethylidene)amino]-3-acetamido-2-[(1R,2R)-1,2,3-trihydroxypropyl]-3,4-dihydro-2H-pyran-6-carboxylic acid redox derivatives.

5 Claims, No Drawings

(56) References Cited

OTHER PUBLICATIONS

International Search Report and Written Opinion mailed Sep. 15, 2010 for International Application No. PCT/GB2010/050797 (12 pages).

International Preliminary Report on Patentability mailed Nov. 24, 2011 for International Application No. PCT/GB2010/050797 (9 pages).

Examination Report mailed Mar. 26, 2014 for corresponding New Zealand Application No. 610978 (2 pages).

* cited by examiner

REDOX DRUG DERIVATIVES

This application is the U.S. national stage application of International (PCT) Patent Application Serial No. PCT/GB2010/050797, filed May 17, 2010, which claims the benefit of GB Application No. 0908338.7, filed May 15, 2009, and GB Application No. 1006112.5, filed Apr. 13, 2010. The entire disclosure of each of these applications is hereby incorporated by reference.

The present invention relates to redox drug derivatives. In particular, the present invention relates to 9-fluoro-2,3-dihydro-3-methyl-10-(4-methyl-1-piperazinyl)-7-oxo-7H-pyrido[1,2,3-de]-1,4-benzoxazine-6-carboxylic acid (ofloxacin), 1-ethyl-6-fluoro-1,4-dihydro-7-(4-methyl-1-piperazinyl)-4-oxo-3-quinolinecarboxylic acid (pefloxacin), (3R,4R,5S)-4-(acetylamino)-5-amino-3-(1-ethylpropoxy)-1-cyclohexene-1-carboxylic acid ethyl ester (oseltamivir), (3S)-3-(aminomethyl)-5-methylhexanoic acid (pregabalin), (3S)-1-[2-(2,3-dihydro-5-benzofuranyl)ethyl]-α-α-diphenyl-3-pyrrolidineacetamide (darifenacin), (1S,2S,3S,4R)-3-[(1S)-1-acetamido-2-ethyl-butyl]-4-(diaminomethylideneamino)-2-hydroxy-cyclopentane-1-carboxylic acid (peramivir) and (2R,3R,4S)-4-[(diaminomethylidene)amino]-3-acetamido-2-[(1R,2R)-1,2,3-trihydroxypropyl]-3,4-dihydro-2H-pyran-6-carboxylic acid (zanamivir) redox derivatives.

Ofloxacin was first disclosed in EP 0 047 005 and U.S. Pat. No. 4,382,892. This disclosure included a racemic mixture of the two enantiomers of ofloxacin. The optically active enantiomer was disclosed in EP 0 206 283. Pefloxacin was first disclosed in DE 2840910 and U.S. Pat. No. 4,292,317. An essential feature of the compounds disclosed in each of these documents is the substitution at the 6-position by a carboxylic acid and at the 7-position by an oxo group. Thus, it is considered that the specific substitution at the b- and 7-positions of the ring is central to providing the desired antibacterial activity properties of the compounds. Moreover the synthetic route for ofloxacin disclosed in EP 0 047 005 involves the conversion of a 4-aza-chromane compound to the below illustrated di-ester compound which is subsequently ring-closed to form an ofloxacin precursor:

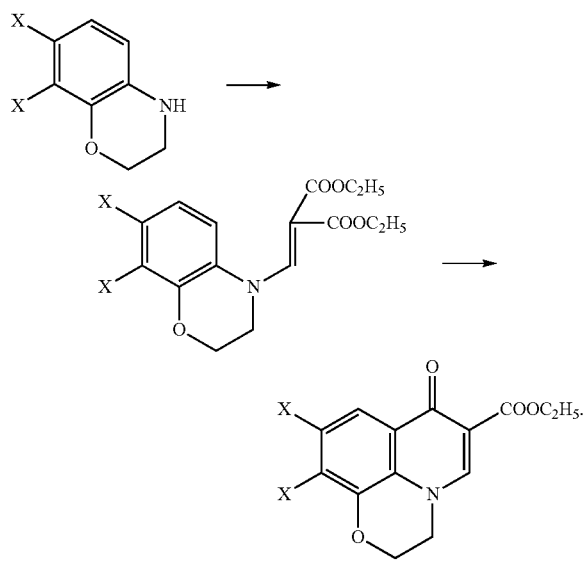

Thus, in addition to being considered essential to providing the desired antibacterial activity properties of the compounds, this specific substitution results from the synthesis of the active compound.

Oseltamivir was first disclosed in U.S. Pat. No. 5,763,483. It appears that the combination of (i) an ester group at the double bond on the cyclohexene ring, and (ii) an amine group para to the ester are essential in obtaining an active compound.

Pregabalin was first disclosed in U.S. Pat. No. 5,563,175 in which its use, amongst other 3-alkyl-4-aminobutyric acid analogues, as an anticonvulsant was also disclosed. In addition to this document, U.S. Pat. No. 6,001,876 and U.S. Pat. No. 6,127,418 disclose a series of 3-alkyl-4-aminobutyric acid analogues which are useful in the treatment of pain and in preventing and treating gastrointestinal damage respectively. The essential features of the compounds disclosed in each of the above documents are the terminal amine group and the opposing terminal carboxylic acid group. Thus, it is considered that these features are essential for providing the desired GABA regulating activity of the compounds which is believed to be responsible for the useful effects of these compounds.

Darifenacin, and its activity as a muscarinic receptor antagonist, was first disclosed in U.S. Pat. No. 5,096,890. This document discloses, in particular, compounds having an amide group adjacent to the two phenyl rings. There are also disclosed compounds having a nitrile group adjacent to the two phenyl rings, the nitrile moiety being in place of the amide moiety. However, it is considered that the presence of the amide group is essential in imparting the antagonistic activity of these compounds as it is disclosed that the analogous nitrile compound is useful as a synthetic intermediate but has low activity as a muscarinic receptor antagonists.

Zanamivir was first disclosed in U.S. Pat. No. 5,360,817. It appears that the combination of (i) a carboxylic acid group at the double bond on the cyclohexene ring, and (ii) an amine group para to the carboxylic acid group are essential in obtaining an active compound.

The acid forms of the parent compounds, for example ofloxacin, pefloxacin and pregabalin, may suffer problems in terms of stability over an extended period of time. For example, oxfloxacin and pefloxacin may undergo decarboxylation of the terminal acid. This represents a significant problem during manufacture of an active principal or during extended storage of the same in a pharmacy. Similarly, the unprotected amide form of darifenacin is subject to hydrolysis to the carboxylic acid derivative. The resulting decomposition products may have reduced activity and potentially increased toxicity when compared with the parent active.

It is therefore an aim of the present invention to provide reduced or oxidised derivatives of active compounds which are able to demonstrate similar to or better than the parent active compound. It is also an aim of the present invention to provide compounds which have an IC50 value comparable to or better than that of the parent active. Ideally, these reduced or oxidised derivatives will have good stability and bioavailability relative to the parent active compound. It is thus an aim to provide reduced or oxidised derivatives having improved stability. Ideally, the reduced or oxidised derivatives will have an extended shelf-life. It is thus an aim of the present invention to provide further compounds having improved bioavailability.

This invention provides compounds that achieve one or more of the above aims. The compounds may be active in their own right or may metabolise or react in aqueous media to yield a parent active compound.

According to a first aspect, the present invention provides a method of preparing an oxidised or reduced pharmaceutical active derivative, comprising:
(i) obtaining a parent pharmaceutical active;
(ii) oxidising the parent pharmaceutical active to provide an oxidised pharmaceutical active derivative which is in an oxidation state one or more oxidation states higher than the parent pharmaceutical active; or reducing the parent pharmaceutical active to provide a reduced pharmaceutical active derivative which is in an oxidation state one or more oxidation states lower than the parent pharmaceutical active; and
(iii) isolating the oxidised or reduced pharmaceutical active derivative.

The term derivative in this context means a compound that is identical to a target active compound (which may be an approved drug compound or a known active structural compound of the same class as an approved drug compound) in terms of its structure except that one or more functional groups in the compound have been oxidised or reduced.

This approach is novel and the finding of activity for compounds of the invention is contrary to normal expectations in the pharmaceutical industry. Whilst, it is may be conventional in the industry to aim to provide prodrugs of certain compounds, the industry has been very wary of modifying active compounds to any significant degree. In addition, there is a concern in the industry that compounds such as aldehydes could be potentially problematic in terms of their effects. Thus aldehydes, acetal, hemi-acetals and related compounds in the same oxidation state as these have been avoided since it is expected that they will not be viable development candidates. Surprisingly, we have found that we can provide active compounds or compounds that metabolise to active compounds by modifying the oxidation state of certain key functional groups in known active compounds. This effect is surprising given that the modification of the oxidation state of one or more functional groups in a known active will inevitably have an effect on the electronic distribution and hence binding of a molecule. Similarly, the overall stereochemistry is likely to be affected which will also affect binding of a molecule at the target receptor site. Thus the finding of activity in the compounds of the invention is both unpredictable and unexpected.

For a compound to qualify as a parent pharmaceutical active drug compound that is suitable for synthetic modification according to the invention, the parent must contain one or more oxidisable or reducible functional groups. Another, requirement of the parent compound is that it must have existing pharmaceutical activity against a particular target. The parent compound is preferably and approved drug. Preferably, the oxidisable or reducible functional group is selected from the group comprising: hydroxyl, carbonyl, carboxylate, amine, amide, imine, and ester. The compound according to the invention will, in one embodiment, thus contain at least one functional group that can be obtained by or has been obtained by reducing or oxidising (as chemically appropriate) one or more groups in the parent active compound selected from the group comprising: hydroxyl, carbonyl, carboxylate, amine, amide, imine, and ester. Most preferred are compounds of the invention derived from a parent having one or more of: hydroxyl, carbonyl, and carboxylate groups.

The efficacy of the compounds of the invention against a particular target can be demonstrated for example by in silico modelling, or by conventional in vitro or in vivo testing. The in silico modelling provides a good proof of efficacy of the compounds of the invention.

In an embodiment, step (ii) of the method comprises oxidising the parent pharmaceutical active to provide an oxidised pharmaceutical active derivative.

In an embodiment, step (ii) of the method comprises reducing the parent pharmaceutical active to provide a reduced pharmaceutical active derivative.

Processes for the manufacture of parent pharmaceutical active are disclosed in EP 0 206 283, U.S. Pat. No. 4,292,317, U.S. Pat. No. 5,763,483, U.S. Pat. Nos. 5,563,175 and 5,096, 890 and, in particular, in the examples of these documents. The disclosures of EP 0 206 283, U.S. Pat. No. 4,292,317, U.S. Pat. No. 5,763,483, U.S. Pat. Nos. 5,563,175, 5,096,890 and U.S. Pat. No. 5,360,817 insofar as the synthetic procedures are concerned form part of the disclosure of the present invention. In the interests of brevity, the details of these synthetic procedures are not reproduced here but it is intended that this subject matter is specifically incorporated into the disclosure of these documents by reference.

Each of the compounds of the present invention may be used as a medicament.

The compounds of the present invention may be used in the treatment of treatment of bacterial infections. For example, diseases such as pneumonia, urinary tract infections, acute bacterial sinusitis, acute bacterial exacerbation of chronic bronchitis, anthrax, various skin infections, chronic bacterial prostatitis, acute pyelonephritis.

The compounds of the present invention may also be used in the treatment of conditions treatable by neuraminidase inhibition. For example, the compounds of the present invention may be used to treat viral infections, in particular, infections caused by the influenza virus.

The compounds of the present invention may also be used in treating conditions treatable by modulating GABA turnover and, in particular, in the treatment of neuropathic pain such as neuropathic pain from diabetic neuropathy or post herpetic neuralgia. The compounds of the present invention may also be used in the treatment of seizures. The compounds of the present invention may also be used in various anxiety disorders, such as bipolar disorder or generalised depression.

The compounds of the present invention may also be used in conditions treatable by blocking the $M_3$-muscarinic acetylcholine receptor. In particular, the compounds of the present invention may also be used in the treatment of urinary incontinence, oesophageal achalasia, irritable bowel syndrome and chronic obstructive airways disease.

The skilled man will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", R C Larock, Wiley-VCH (1999 or later editions), "March's Advanced Organic Chemistry—Reactions, Mechanisms and Structure", M B Smith, J. March, Wiley, (5th edition or later) "Advanced Organic Chemistry, Part B, Reactions and Synthesis", F A Carey, R J Sundberg, Kluwer Academic/Plenum Publications, (2001 or later editions), "Organic Synthesis—The Disconnection Approach", S Warren (Wiley), (1982 or later editions), "Designing Organic Syntheses" S Warren (Wiley) (1983 or later editions), "Guidebook To Organic Synthesis" R K Mackie and D M Smith (Longman) (1982 or later editions), etc., and the references therein as a guide.

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein.

Compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

According to a second aspect, the present invention provides a compound of formula I:

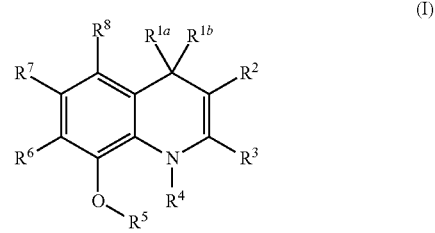

wherein:

$R^{1a}$ and $R^{1b}$ are together selected from the group comprising: oxo and =NOR"; or $R^{1a}$ is —H and $R^{1b}$ is —OR"; and $R^2$ is selected from the group comprising: —COOR", —CR"O, —CR"R"OR", —CR"=NOR'" and

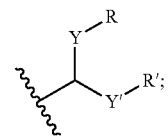

wherein

—Y— is selected from the group comprising: =N—, —O— and —S—;

—Y'— is selected from the group comprising: —O— and —S—;

each R, R' and R" is independently selected from the group comprising: —H and $C_{1-4}$ alkyl; or each R" is independently selected from the group comprising: —H and $C_{1-4}$ alkyl, and R and R' join to form a 5 to 8 membered ring together with the atoms to which they are bonded; and R'" is selected from the group comprising: H, $C_{1-4}$ alkyl and —(CR""R"")$_n$—aryl; wherein each R"" is independently selected from the group comprising: H and aryl and wherein n is from 1 to 4;

$R^3$, $R^7$ and $R^8$ are each independently selected from the group comprising: H, substituted or unsubstituted $C_{1-4}$ alkyl and halogen;

$R^4$ and $R^5$ are each independently substituted or unsubstituted $C_{1-4}$ alkyl; or $R^4$ and $R^5$ join to form a 6 membered ring together with the atoms to which they are bonded;

$R^6$ is a substituted or unsubstituted N-heterocycloalkyl group comprising from 5 to 10 ring atoms and at least one nitrogen atom;

wherein, where chemically possible, each alkyl and each aryl may be independently substituted with up to 5 substituents independently selected from the group comprising: F, Cl, Br, CN, NO$_2$, OR" or OH; and provided that the compound is not

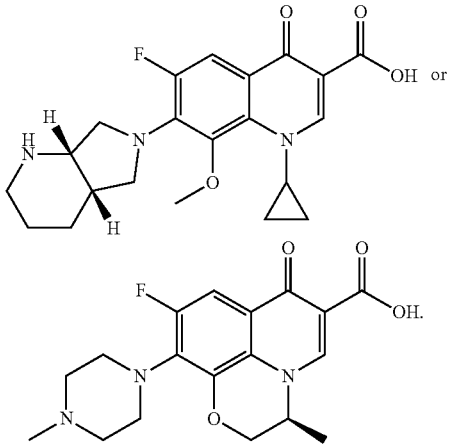

According to a third aspect, the present invention provides a compound of formula (Ia):

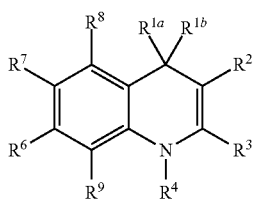

(Ia)

wherein:
R$^{1a}$ and R$^{1b}$ are together selected from the group comprising: oxo and =NOR"; or R$^{1a}$ is —H and R$^{1b}$ is —OR"; and
R$^2$ is selected from the group comprising: —COOR", —CR"O, —CR"R"OR", —CR"=NOR'" and

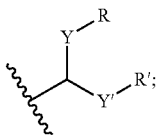

wherein
—Y— is selected from the group comprising: =N—, —O— and —S—;
—Y'— is selected from the group comprising: —O— and —S—;
each R, R' and R" is independently selected from the group comprising: —H and C$_{1-4}$ alkyl; or each R" is independently selected from the group comprising: —H and C$_{1-4}$ alkyl, and R and R' join to form a 5 to 8 membered ring together with the atoms to which they are bonded; and
R'" is selected from the group comprising: H, C$_{1-4}$ alkyl and —(CR""R"")$_n$—aryl; wherein R"" is selected from the group comprising: H and aryl;
R$^3$, R$^7$, R$^8$ and R$^9$ are each independently selected from the group comprising: H, substituted or unsubstituted C$_{1-4}$alkyl and halogen;

R$^4$ is a substituted or unsubstituted C$_{1-4}$alkyl;
R$^6$ is a substituted or unsubstituted N-heterocycloalkyl group comprising from 5 to 10 ring atoms and at least one nitrogen atom;
wherein, where chemically possible, each alkyl and each aryl may be independently substituted with up to 5 substituents independently selected from the group comprising: F, Cl, Br, CN, NO$_2$, OR" or OH; and provided that the compound is not

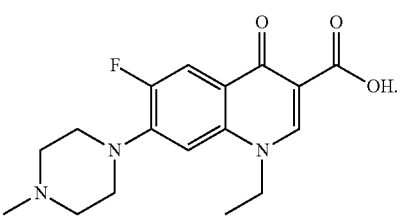 [SMILES: CCn1cc(C(=O)O)c(=O)c2cc(F)c(N3CCN(C)CC3)cc21]

The following embodiments apply to the compounds of the above second and third aspects.
In an embodiment, when R$^{1a}$ and R$^{1b}$ together are oxo, R$^2$ is not —COOH.
In an embodiment, R$^{1a}$ and R$^{1b}$ are together oxo. In an alternative embodiment, R$^{1a}$ and R$^{1b}$ are together =NOR". Preferably, R$^{1a}$ and R$^{1b}$ are together =NOH. In an alternative embodiment, R$^{1a}$ is H and R$^{1b}$ is —OR". Preferably, R$^{1a}$ is H and R$^{1b}$ is —OH.
In an embodiment, R$^2$ is selected from the group comprising: —COOR", —CR"O and —CR"R"OR". Preferably, R$^2$ is selected from the group comprising: —COOH, —CR"O and —CR"R"OH. In an alternative embodiment, R$^2$ is —CR"=NOR'", e.g. —CH=NOCH$_2$Ph, —CH=NOC$_2$H$_5$, —CH=NOCPh$_3$,

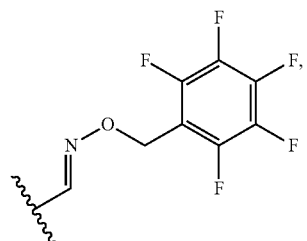

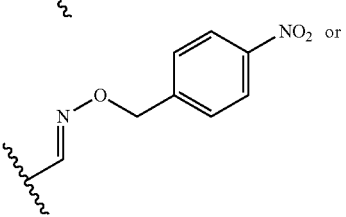

Preferably, R$^2$ is —CR"=NOH. Preferably, each R" is H.
In an embodiment, R$^3$ is H.
In an embodiment, R$^4$ is substituted or unsubstituted C$_{1-3}$alkyl. In an embodiment, R$^4$ is substituted or unsubstituted cyclopropyl, preferably unsubstituted cyclopropyl. In an alternative embodiment, R$^4$ is substituted or unsubstituted ethyl.

In an embodiment, $R^5$ is substituted or unsubstituted $C_{1-3}$alkyl. In an embodiment, $R^5$ is methyl.

In an embodiment, $R^4$ is ethyl and $R^5$ is methyl and $R^4$ and $R^5$ join to form a 6 membered ring together with the atoms to which they are bonded.

In an embodiment, $R^6$ is a substituted or unsubstituted N-heterocycloalkyl group comprising from 5, 6, 7, 8, 9 or 10 ring atoms and at least one nitrogen atom. Preferably, the N-heterocycloalkyl group comprises at least two nitrogen atoms. In an embodiment, $R^6$ is substituted or unsubstituted piperizine, preferably N-methyl piperizine. In an embodiment, $R^6$ is substituted or unsubstituted group of

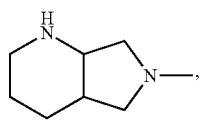

preferably unsubstituted.

In an embodiment, $R^7$ is halogen. Preferably, $R^7$ is fluoro.
In an embodiment, $R^8$ is hydrogen.
In an embodiment, $R^3$ is H, $R^7$ is fluoro and $R^8$ is hydrogen.
In an embodiment, $R^4$ is cyclopropyl, $R^5$ is methyl and $R^6$ is

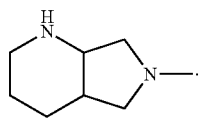

In an embodiment, $R^4$ is ethyl, $R^5$ is methyl, and $R^4$ and $R^5$ join to form a 6 membered ring together with the atoms to which they are bonded, and $R^6$ is N-methyl piperizine.

In an embodiment, $R^3$ is H, $R^4$ is cyclopropyl, $R^5$ is methyl, $R^6$ is

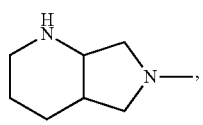

$R^7$ is fluoro and $R^8$ is hydrogen.

In an embodiment, $R^3$ is H, $R^4$ is ethyl, $R^5$ is methyl, and $R^4$ and $R^5$ join to form a 6 membered ring together with the atoms to which they are bonded, $R^6$ is N-methyl piperizine, $R^7$ is fluoro and $R^8$ is hydrogen.

In an embodiment, R" is H.
In an embodiment, the ring formed by the R and R' in

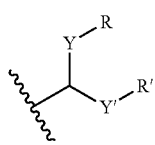

is a 5 to 7 membered ring, preferably a 5 or 6 membered ring.

In an embodiment, Y and Y' are each —O—. In an alternative embodiment, Y and Y' are each —S—. In a further alternative embodiment, Y is —O— and Y' is —S—. In another embodiment, Y is =N— and Y' is —O—. In another embodiment, Y is =N— and Y' is —S—.

In an embodiment, R is H. In an embodiment, R' is H. In an alternative embodiment, R and R' are each $C_{1-3}$alkyl, e.g. methyl, ethyl or propyl. In an alternative embodiment, one of R and R' is H and the other is $C_{1-3}$alkyl, e.g. methyl, ethyl or propyl.

In an embodiment, Y, Y', R and R' are selected from the following table:

| Y | Y' | R | R' |
|---|---|---|---|
| —O— | —O— | H | H |
| —S— | —O— | H | H |
| —S— | —S— | H | H |
| =N— | —O— | H | H |
| =N— | —S— | H | H |
| —O— | —O— | Methyl | H |
| —O— | —O— | Ethyl | H |
| —O— | —O— | Propyl | H |
| —S— | —O— | Methyl | H |
| —S— | —O— | Ethyl | H |
| —S— | —O— | Propyl | H |
| =N— | —O— | Methyl | H |
| =N— | —O— | Ethyl | H |
| =N— | —O— | Propyl | H |
| —O— | —S— | Methyl | H |
| —O— | —S— | Ethyl | H |
| —O— | —S— | Propyl | H |
| —S— | —S— | Methyl | H |
| —S— | —S— | Ethyl | H |
| —S— | —S— | Propyl | H |
| =N— | —S— | Methyl | H |
| =N— | —S— | Ethyl | H |
| =N— | —S— | Propyl | H |
| —O— | —O— | Methyl | $C_{1-3}$alkyl |
| —O— | —O— | Ethyl | $C_{1-3}$alkyl |
| —O— | —O— | Propyl | $C_{1-3}$alkyl |
| —S— | —O— | Methyl | $C_{1-3}$alkyl |
| —S— | —O— | Ethyl | $C_{1-3}$alkyl |
| —S— | —O— | Propyl | $C_{1-3}$alkyl |
| =N— | —O— | Methyl | $C_{1-3}$alkyl |
| =N— | —O— | Ethyl | $C_{1-3}$alkyl |
| =N— | —O— | Propyl | $C_{1-3}$alkyl |
| —O— | —S— | Methyl | $C_{1-3}$alkyl |
| —O— | —S— | Ethyl | $C_{1-3}$alkyl |
| —O— | —S— | Propyl | $C_{1-3}$alkyl |
| —S— | —S— | Methyl | $C_{1-3}$alkyl |
| —S— | —S— | Ethyl | $C_{1-3}$alkyl |
| —S— | —S— | Propyl | $C_{1-3}$alkyl |
| =N— | —S— | Methyl | $C_{1-3}$alkyl |
| =N— | —S— | Ethyl | $C_{1-3}$alkyl |
| =N— | —S— | Propyl | $C_{1-3}$alkyl | wherein $C_{1-3}$alkyl includes methyl, ethyl and propyl.

In an embodiment, the compound of formula I is selected the group comprising:

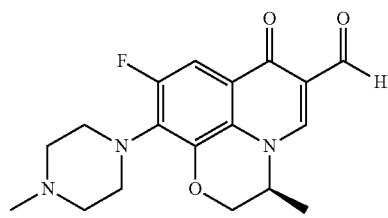

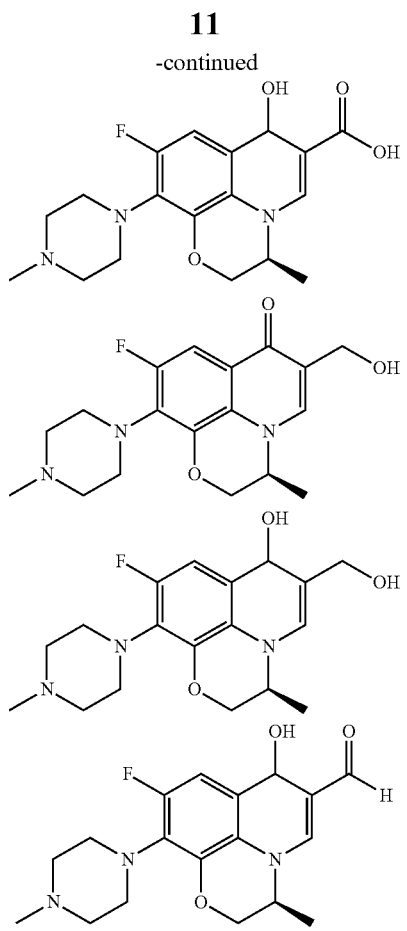
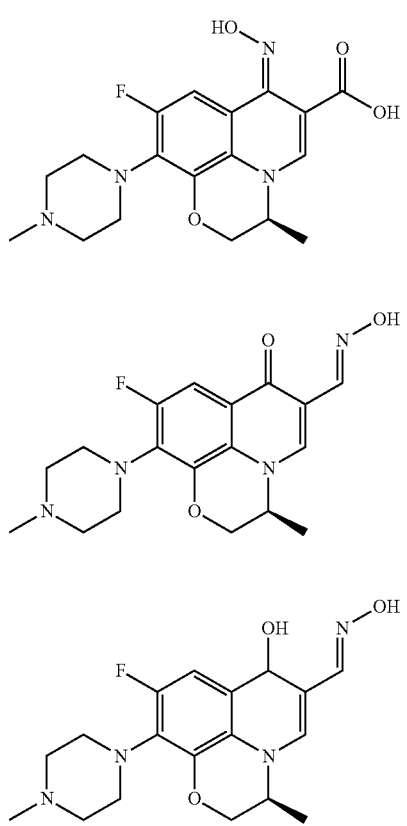
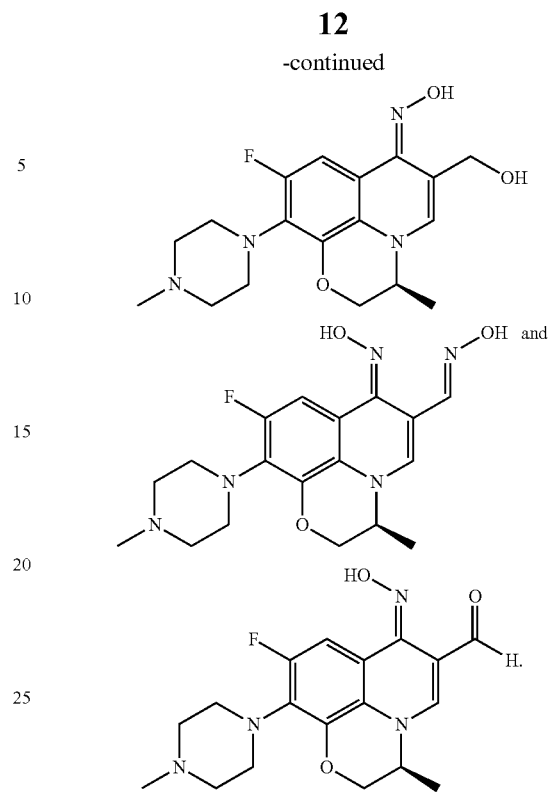
In an embodiment, the compound of formula I is selected the group comprising:
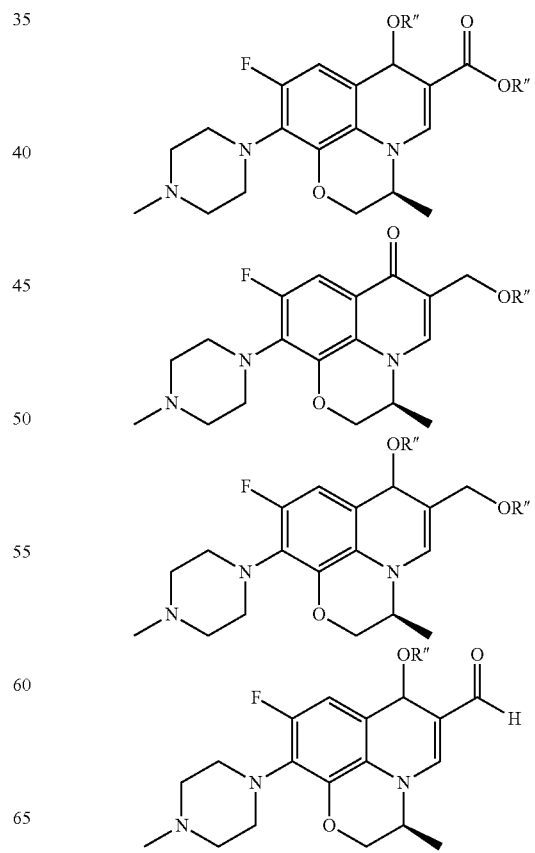

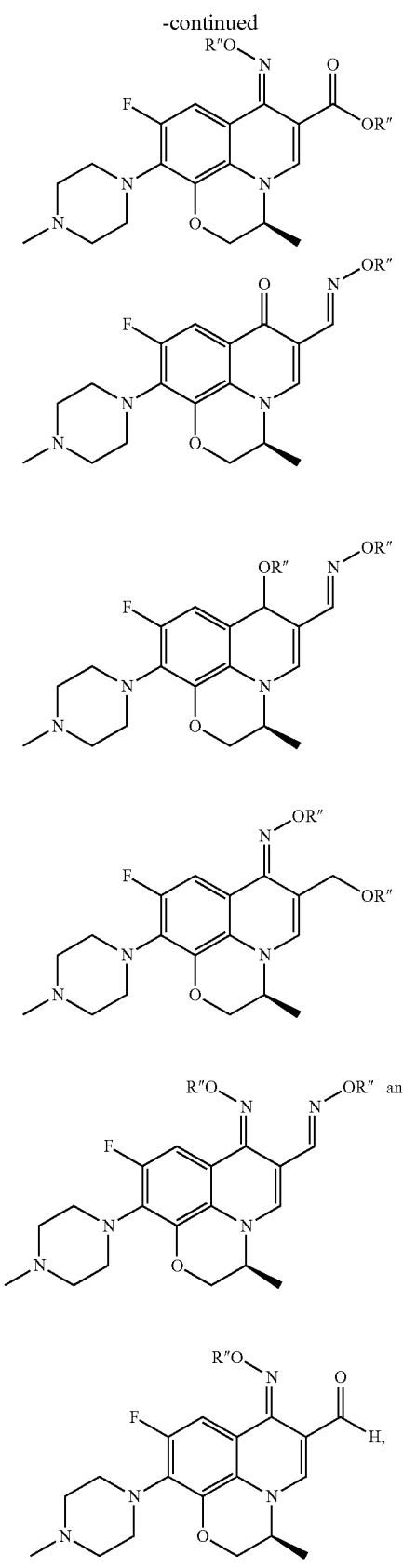
wherein R″ is as defined above.
In an embodiment, the compound of formula I is selected the group comprising:
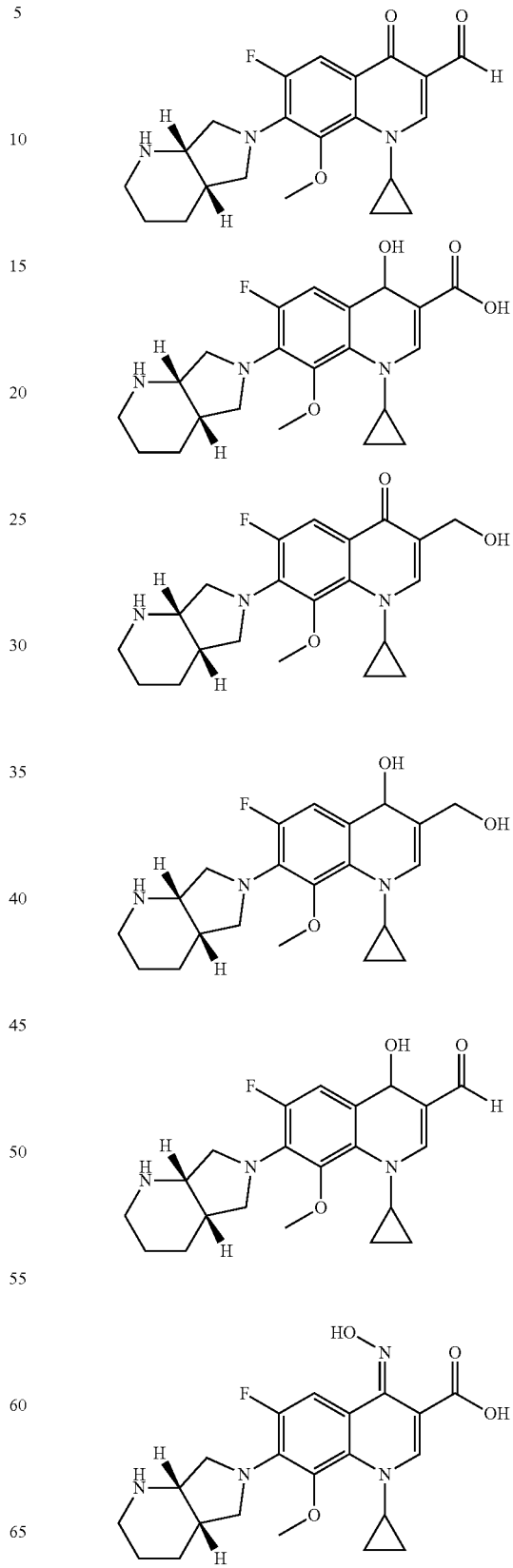

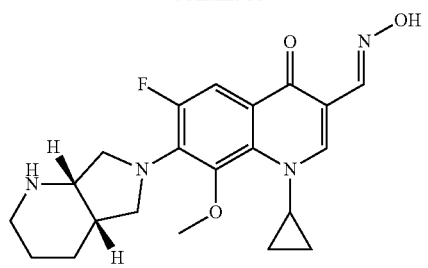
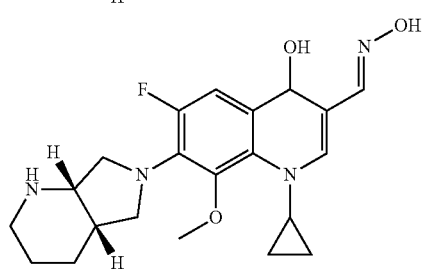
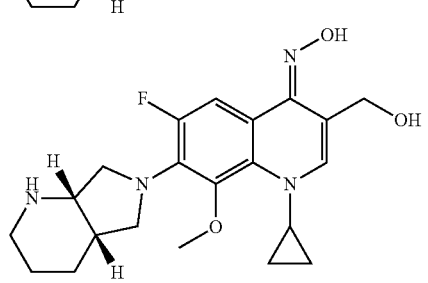
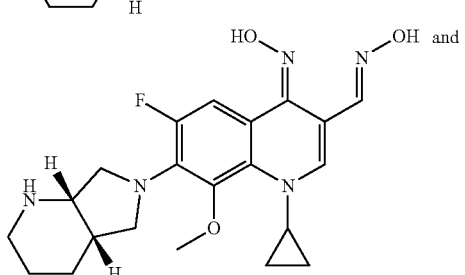
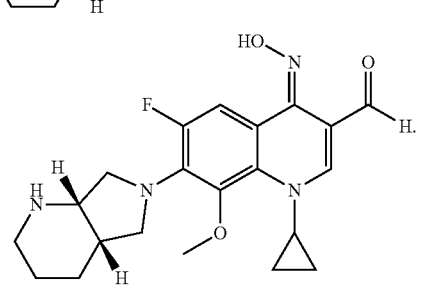
In an embodiment, the compound of formula I is selected the group comprising:
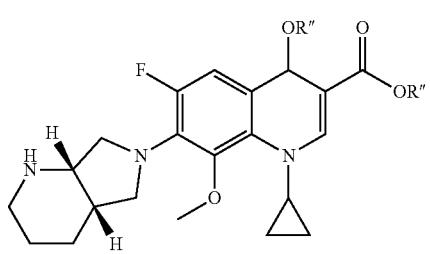
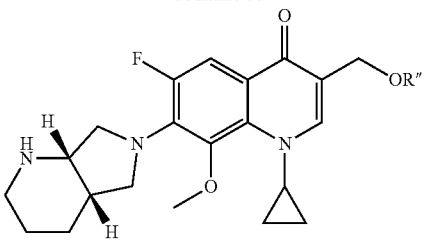
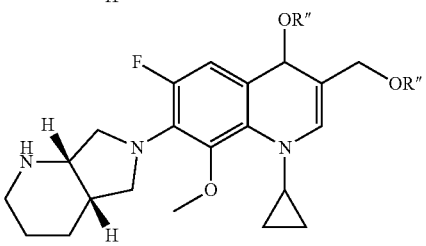
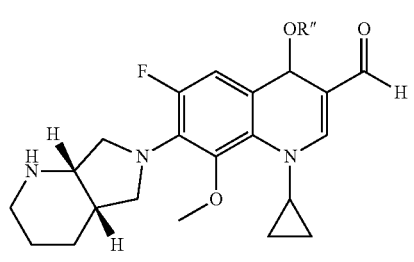
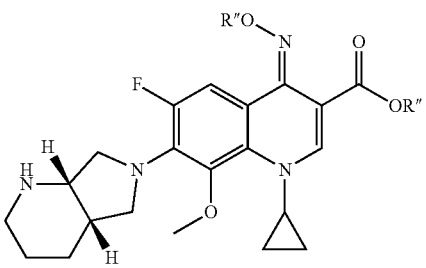
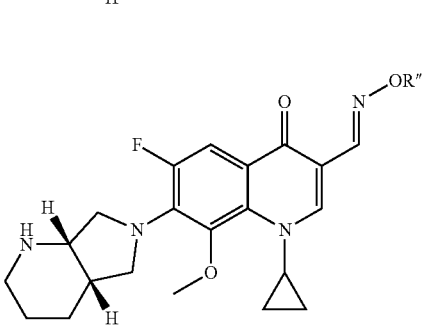
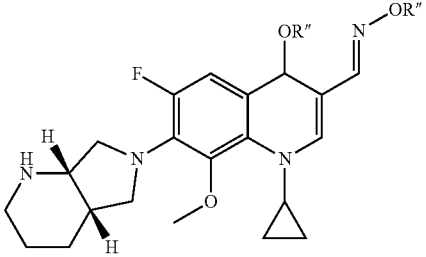

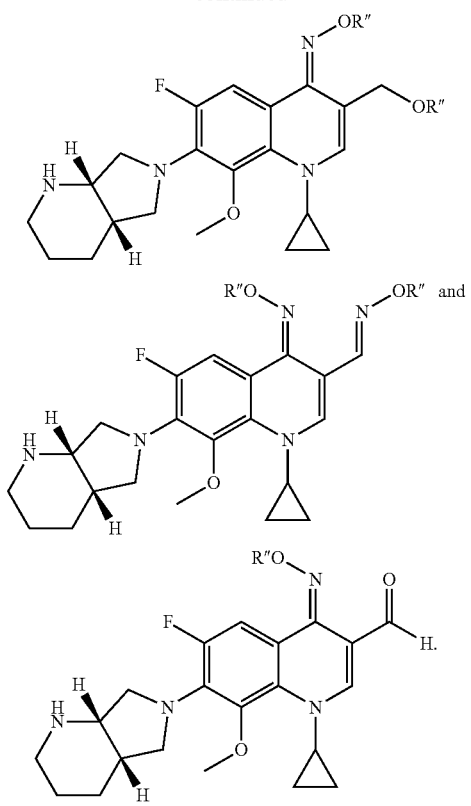
In an embodiment, the compound of formula I is selected the group comprising:
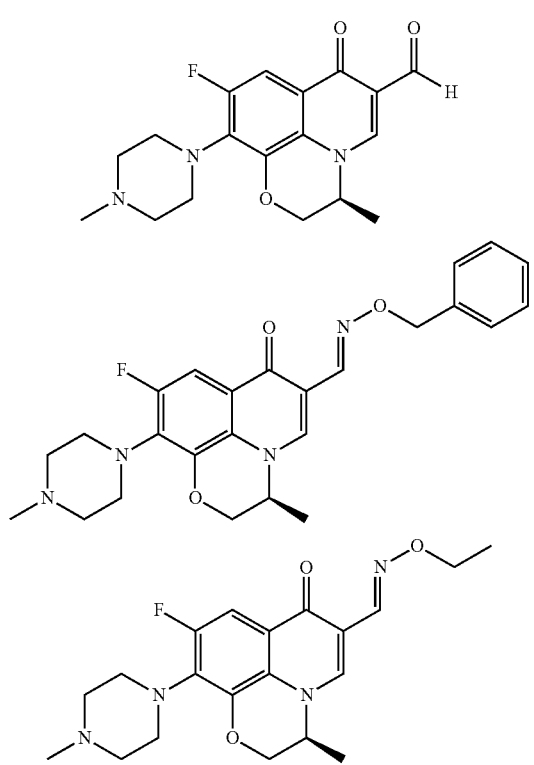
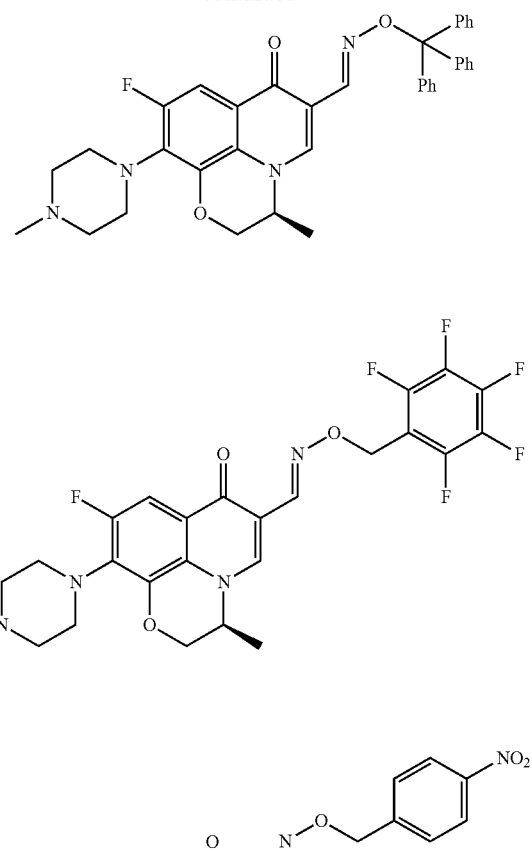
In an embodiment, the compound of formula Ia is selected the group comprising:
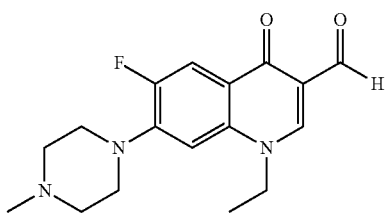

-continued

According to a fourth aspect, the present invention provides a compound of formula II:

wherein:
R$^{11}$ is selected from the group comprising: —C(O)NR"R'",
—CR"R"OR", —COO(C$_{1-3}$alkyl), —CR"O,
—CR'"=NOR" and wherein
—Y— is selected from the group comprising: =N—,
—O— and —S—;
—Y'— is selected from the group comprising: —O— and —S—; and
each R, R' and R" is independently selected from the group comprising: —H, C$_{1-4}$ alkyl and —(CH$_2$)$_n$-aryl; or each R" is independently selected from the group comprising: —H, C$_{1-4}$ alkyl and —(CH$_2$)$_n$-aryl, and R and R' join to form a 5 to 8 membered ring together with the atoms to which they are bonded, wherein n is from 1 to 4;
each R'" is selected from the group comprising: H, C$_{1-4}$ alkyl, OR" and SR"; and
each R"" is selected from the group comprising: H, OH and SH;
R$^{12}$ and R$^{16}$ are each independently selected from the group comprising: H, substituted or unsubstituted C$_{1-4}$alkyl and halogen;
R$^{13}$ is selected from the group comprising: —OR",
—NR"R" and —(CR"R")$_m$NR"R", wherein m is 1 or 2;
R$^{14}$ is selected from the group comprising:
—NR"CO(C$_{1-3}$alkyl) and —N=CR"(C$_{1-3}$alkyl);
R$^{15}$ is substituted or unsubstituted C$_{1-8}$alkyl;
X is O or S;
wherein, where chemically possible, each alkyl may be substituted with up to 5 substituents independently selected from the group comprising: F, Cl, Br, CN, NO$_2$, OR" or OH; and provided that the compound is not In an embodiment, when R$^{11}$ is —COOEt, R$^{14}$ is not —NHCOMe.
In an embodiment, R$^{11}$ is —COO(C$_{1-3}$alkyl). In an embodiment, the C$_{1-3}$alkyl is unsubstituted. Preferably, the C$_{1-3}$alkyl is methyl or ethyl, more preferably ethyl. In an alternative embodiment, R$^{11}$ is —CR"O. Preferably R" is H. In another alternative embodiment, R$^{11}$ is —CH$_2$OH. In another alternative embodiment, R$^{11}$ is —CR'"=NOR". Preferably R'" is H. Preferably, R$^{11}$ is —CSR"=NOR". Preferably, R$^{11}$ is —COR"=NOR". Preferably, R$^{11}$ is —CR'"=NOH. Preferably R" is H. In an another alternative embodiment, R$^{11}$ is In an embodiment, R$^{12}$ is H.
In an embodiment, R$^{13}$ is —NR"R". In an embodiment, R$^{13}$ is —NH$_2$.
In an embodiment, R$^{14}$ is —NR"CO(C$_{1-3}$alkyl). In an alternative embodiment, R$^{14}$ is —N=CR"(C$_{1-3}$alkyl). Preferably, the C$_{1-3}$alkyl is methyl or ethyl, preferably methyl.
In an embodiment, when R$^{14}$ is —NHCOMe, R$^{11}$ is not a group having an acidic hydrogen atom. In this context, an acidic hydrogen is a hydrogen that can be removed by a base yielding an anion or its corresponding salt or solvate more specifically R$^{11}$ is a group having a pKa of more than 10.
In an embodiment, R$^{15}$ is substituted or unsubstituted C$_{1-6}$alkyl. In an embodiment, R$^{15}$ is methyl, ethyl, propyl, butyl, pentyl or hexyl. Preferably, R$^{15}$ is 3-pentyl.
In an embodiment, R$^{16}$ is H.
In an embodiment, R" is H.
In an embodiment, R'" is —OH or —SH. In an alternative embodiment, R'" is H.
In an embodiment, X is O. In an embodiment, X is S.
In an embodiment, R$^{12}$ is H, R$^{13}$ is —NH$_2$, R$^{15}$ is 3-pentyl, R$^{16}$ is H and X is O.
In an embodiment, Y, Y', R and R' are each as defined as in the embodiments of the second aspect for formula I.
In an embodiment, the compound of formula II is selected from the group comprising:

-continued

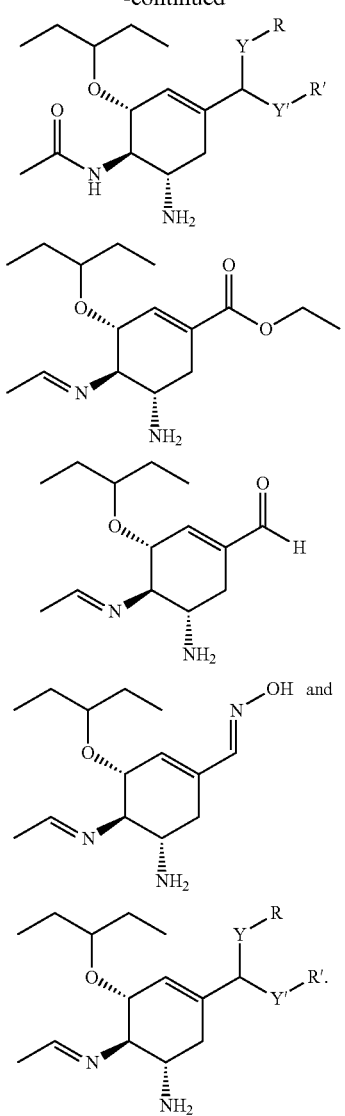

In an embodiment, the compound of formula II is selected from the group comprising:

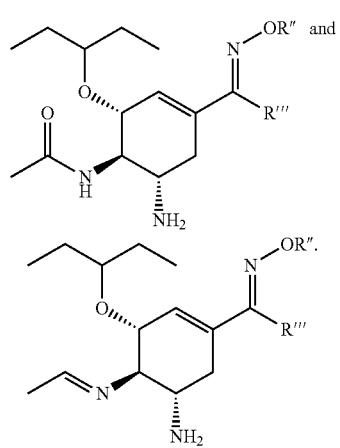

According to a fifth aspect, the present invention provides a compound of formula III:

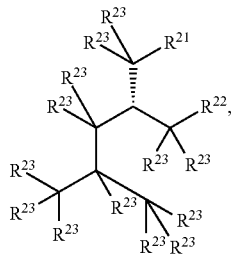

wherein:
each $R^{23}$ is independently selected from the group comprising: —H, —Cl, —F and $C_{1-3}$ alkyl;
$R^{21}$ is —NRR'; and
$R^{22}$ is selected from the group comprising: —CR"O, —CR"=NOR''', —N(=NR")R", CR"R"OR" and

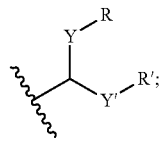

wherein:
—Y— is selected from the group comprising: =N—, —O— and —S—;
—Y'— is selected from the group comprising: —O— and —S—;
each R, R' and R" is independently selected from the group comprising: —H and $C_{1-4}$ alkyl; or each R" is independently selected from the group comprising: —H and $C_{1-4}$ alkyl, and R and R' join to form a 5 to 8 membered ring together with the atom(s) to which they are bonded; and
R''' is selected from the group comprising: H, $C_{1-4}$ alkyl and —(CR''''R''')$_n$— aryl; wherein R'''' is selected from the group comprising: H and aryl and wherein n is from 1 to 4;
or
wherein $R^{21}$ is —N= and $R^{22}$ is —CR"= and $R^{21}$ and $R^{22}$ join to form a 5 membered ring together with the atoms to which they are bonded; or
wherein $R^{21}$ is —NR"— and $R^{22}$ is —C(O)— and $R^{21}$ and $R^{22}$ join to form a 5 membered ring together with the atoms to which they are bonded.

In an embodiment when $R^{21}$ and $R^{22}$ join to form a 5 membered ring together with the atoms to which they are bonded, the ring may be saturated or unsaturated.

In an embodiment, $R^{21}$ is —N= and $R^{22}$ is —CR"= and $R^{21}$ and $R^{22}$ join to form a 5 membered ring together with the atoms to which they are bonded. Preferably, R" is H.

In an embodiment, $R^{21}$ is —NH$_2$. In an embodiment, $R^{21}$ is

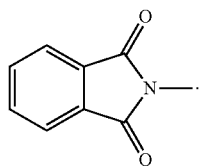

In an embodiment, $R^{21}$ is

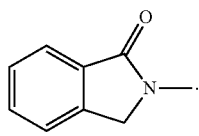

In an embodiment, $R^{22}$ is —CR"O, preferably $R^{22}$ is —CHO. In an alternative embodiment, $R^{22}$ is —CR"=NOR". Preferably, $R^{22}$ is —CR"=NOH, and further preferably $R^{22}$ is —CH=NOH. In an alternative embodiment, $R^{22}$ is CR"R"OH. In an alternative embodiment, $R^{22}$ is

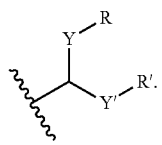

In an alternative embodiment, $R^{22}$ is —N(=NH)R".

In an embodiment, each $R^{23}$ is H.

In an embodiment, each $R^{23}$ is independently selected from the group comprising: —H and —$C_{1-3}$ alkyl, e.g. methyl, ethyl or propyl.

In an embodiment, Y, Y', R and R' are each as defined as in the embodiments of the second aspect for the compounds of formula I.

In an embodiment, the compound of formula III is selected from the group comprising:

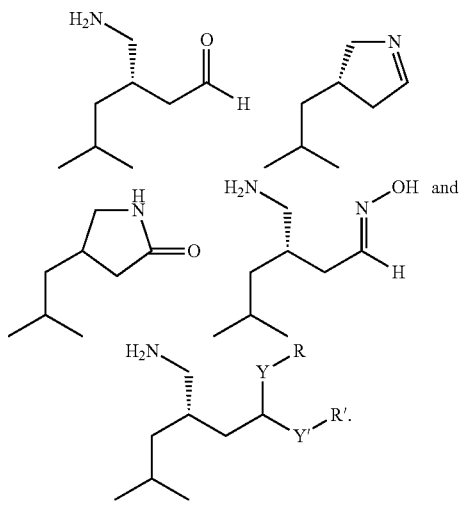

In an embodiment, the compound of formula III is:

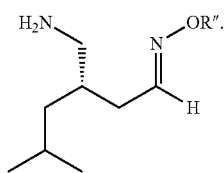

In an embodiment, the compound of formula III is selected from the group comprising:

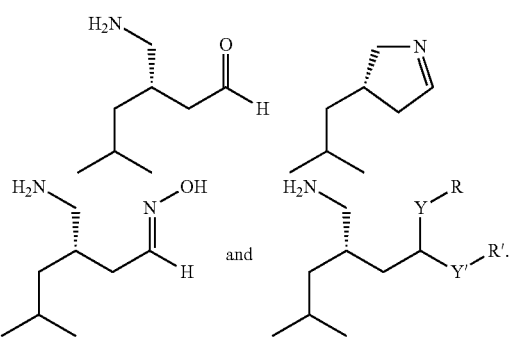

According to a sixth aspect, the present invention provides a compound of formula IV:

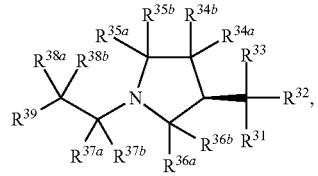

wherein:
$R^{31}$ is selected from the group comprising: —CR"R"OR", —CR"O, —CR"=NR", —CR"=NOR" and

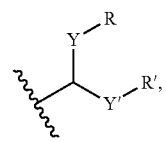

wherein
—Y— is selected from the group comprising: =N—, —O— and —S—;
—Y'— is selected from the group comprising: —O— and —S—; and
each R, R' and R" is independently selected from the group comprising: —H and $C_{1-4}$ alkyl; or each R" is independently selected from the group comprising: —H and $C_{1-4}$ alkyl, and R and R' join to form a 5 to 8 membered ring together with the atoms to which they are bonded;
$R^{32}$ and $R^{33}$ are each independently selected from the group comprising: substituted or unsubstituted phenyl and substituted or unsubstituted pyridinyl;
$R^{34a}$, $R^{34b}$, $R^{35a}$, $R^{35b}$, $R^{36a}$, $R^{36b}$, $R^{37a}$, $R^{37b}$, $R^{38a}$ and $R^{38b}$ are each independently selected from the group comprising: —H, $C_{1-4}$alkyl and halo;
$R^{39}$ is selected from the group comprising: substituted or unsubstituted aryl and substituted or unsubstituted heteroaryl.

In an embodiment, $R^{31}$ is —CHO. In an alternative embodiment, $R^{31}$ is —CR"=NH, preferably —CH=NH. In a further alternative embodiment, $R^{31}$ is —CR"NOH. Preferably, $R^{31}$ is —CH=NOR", more preferably, $R^{31}$ is —CH=NOH. In a further alternative embodiment, $R^{31}$ is —CR"R"OH. In a further alternative embodiment, $R^{31}$ is

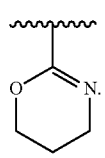

In a further alternative embodiment, $R^{31}$ is

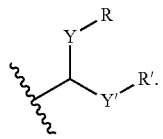

In an embodiment, $R^{32}$ is phenyl.

In an embodiment, $R^{33}$ is phenyl.

In an embodiment, $R^{32}$ and $R^{33}$ are each phenyl.

In an embodiment, $R^{34a}$, $R^{34b}$, $R^{35a}$, $R^{35b}$, $R^{36a}$ and $R^{36b}$ are each selected from the group comprising: —H, -Me and —F. In an embodiment, $R^{34a}$, $R^{34b}$, $R^{35a}$, $R^{35b}$, $R^{36a}$ and $R^{36b}$ are each —H.

In an embodiment, $R^{37a}$, $R^{37b}$, $R^{38a}$ and $R^{38b}$ are each selected from the group comprising: —H, -Me and —F. In an embodiment, $R^{37a}$, $R^{37b}$, $R^{38a}$ and $R^{38b}$ are each —H.

In an embodiment, $R^{32}$ and $R^{33}$ are each phenyl and $R^{34a}$, $R^{34b}$, $R^{35a}$, $R^{35b}$, $R^{36a}$, $R^{36b}$, $R^{37a}$, $R^{37b}$, $R^{38a}$ and $R^{38b}$ are each —H.

In an embodiment, $R^{39}$ is a substituted phenyl ring or bicyclic ring system comprising a fused phenyl ring. In an embodiment, $R^{39}$ is 5-benzo[b]-oxolanyl.

In an embodiment, $R^{32}$ and $R^{33}$ are each phenyl, $R^{34a}$, $R^{34b}$, $R^{35a}$, $R^{35b}$, $R^{36a}$, $R^{37b}$, $R^{38a}$ and $R^{38b}$ are each —H and $R^{39}$ is 5-benzo[b]-oxolanyl.

In an embodiment, Y, Y', R and R' are each as defined as in the embodiments of the second aspect for the compounds of formula I.

In an embodiment, the compound of formula IV is selected from the group comprising:

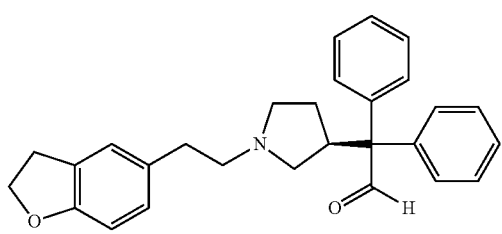

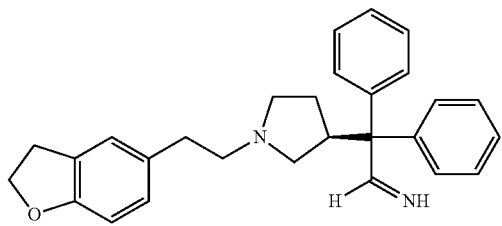

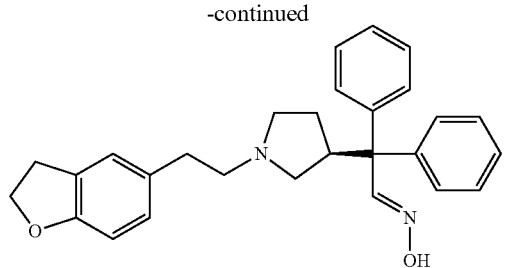

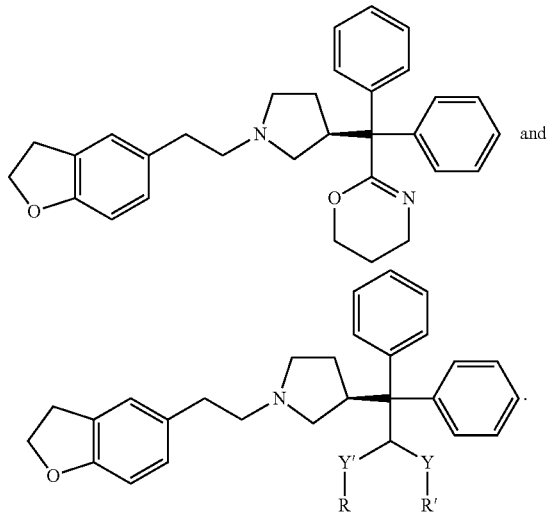

In an embodiment, the compound of formula IV is selected from the group comprising:

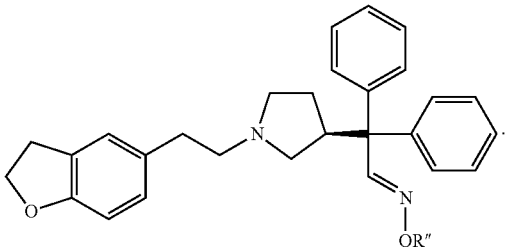

According to a seventh aspect, the present invention provides a compound of formula V:

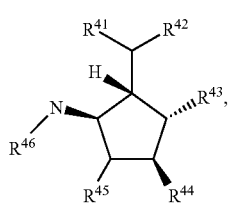

wherein:

$R^{41}$ is selected from the group comprising: —NR"CO($C_{1-3}$alkyl) and —N=CR"($C_{1-3}$alkyl);

$R^{42}$ is substituted or unsubstituted $C_{1-8}$ alkyl;

$R^{43}$ is selected from the group comprising: —OR", —NR"R", —(CR"R")$_m$OR" and —(CR"R")$_m$NR"R", wherein m is 1 or 2;

$R^{44}$ is selected from the group comprising: —COOR", —CR"O, —CR"R"OR", —CR'"=NOR", —C(O)NR"R"" and

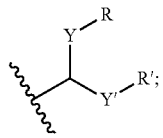

wherein

—Y— is selected from the group comprising: =N—, —O— and —S—;

—Y'— is selected from the group comprising: —O— and —S—;

each R, R' and R" is independently selected from the group comprising: —H and $C_{1-4}$ alkyl; or each R" is independently selected from the group comprising: —H and $C_{1-4}$ alkyl, and R and R' join to form a 5 to 8 membered ring together with the atoms to which they are bonded;

each R'" is selected from the group comprising: H, $C_{1-4}$ alkyl, OR" and SR"; and each R"" is selected from the group comprising: H, OH and SH;

$R^{45}$ is selected from the group comprising: H, substituted or unsubstituted $C_{1-4}$alkyl and halogen; and $R^{46}$ is selected from the group comprising: —C(=NR")NR"R", —C(=O)NR"R" and —C(=O)OR"; provided that the compound is not

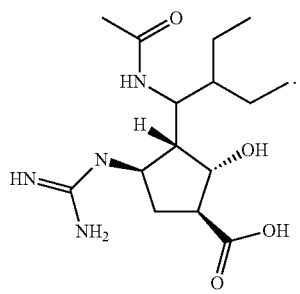 [SMILES: CCC(CC)C(NC(C)=O)[C@@H]1[C@H](O)[C@@H](C(=O)O)C[C@H]1NC(=N)N]

In an embodiment, when $R^{41}$ is —NHCOMe, $R^{44}$ is not —COOH.

In an embodiment, $R^{41}$ is —NR"CO($C_{1-3}$alkyl). In an alternative embodiment, $R^{41}$ is —N=CR"($C_{1-3}$alkyl). Preferably, the $C_{1-3}$alkyl is methyl. Preferably, R" is H.

In an embodiment, $R^{42}$ is $C_{1-6}$ alkyl. Preferably, $R^{42}$ is $C_{3-6}$ alkyl. More preferably, $R^{42}$ is 3-pentyl.

In an embodiment, $R^{43}$ is —OR". Preferably, $R^{43}$ is —OH.

In an embodiment, $R^{44}$ is —COOR". Preferably $R^{44}$ is —COOH. In an alternative embodiment, $R^{44}$ is —CR"O, preferably, —CHO. In an alternative embodiment, $R^{44}$ is —CR"R"OH. In an alternative embodiment, $R^{44}$ is —CR'"=NOR". Preferably, R'" is H. Preferably, $R^{44}$ is —CSR"=NOR". Preferably, $R^{44}$ is —COR"=NOR". Preferably, $R^{44}$ is —CR'"=NOH, more preferably —CH=NOH. Preferably, R" is H. In an alternative embodiment, $R^{44}$ is

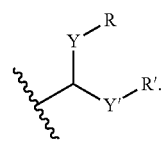

In an embodiment, $R^{45}$ is H.

In an embodiment, $R^{46}$—C(=NR")NR"R", preferably —C(=NH)$NH_2$.

In an embodiment, $R^{42}$ is 3-pentyl, $R^{43}$ is —OH, $R^{45}$ is H and $R^{46}$—C(=NH)$NH_2$.

In an embodiment, the compound of formula V is selected from the group comprising:

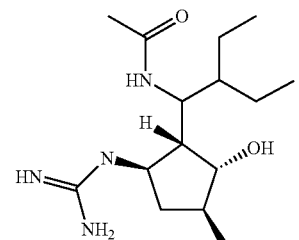

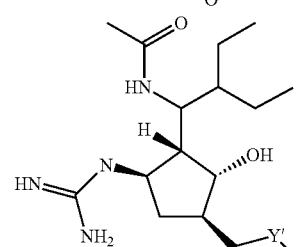

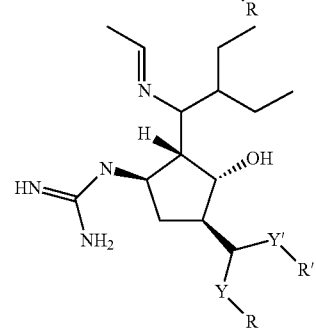

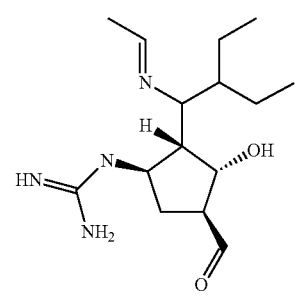

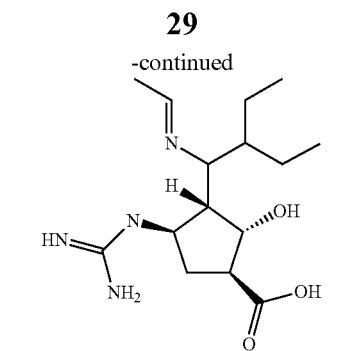
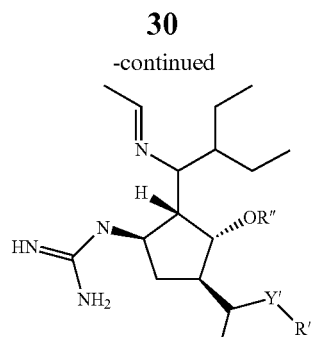
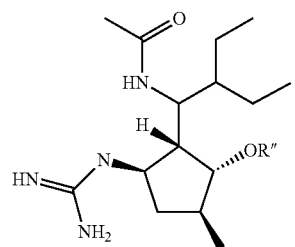
and
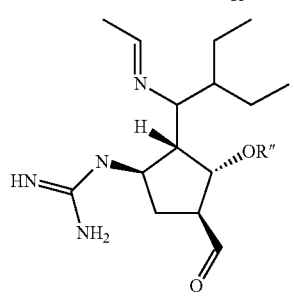
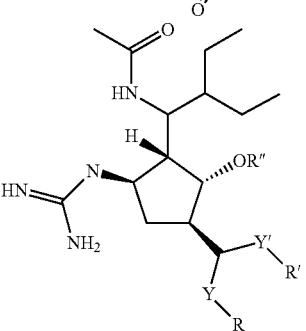
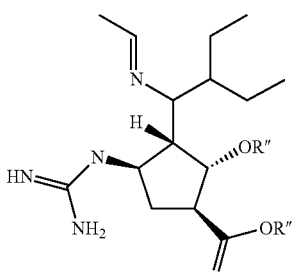
In an embodiment, the compound of formula V is selected from the group comprising:
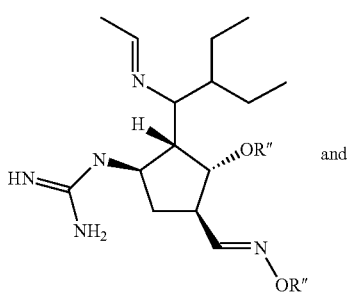
and
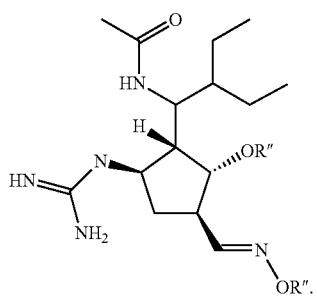

According to an eighth aspect, the present invention provides a compound of formula VI:

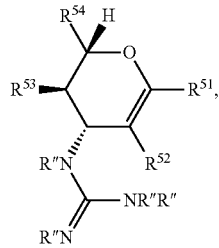

wherein

R$^{51}$ is selected from the group comprising: —C(O)NR"R"", —COOR", —CR"O, —CR"'=NOR" and

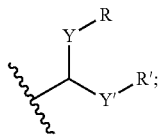

wherein

—Y— is selected from the group comprising: =N—, —O— and —S—;

—Y'— is selected from the group comprising: —O— and —S—;

each R, R' and R" is independently selected from the group comprising: —H and C$_{1-4}$ alkyl; or each R" is independently selected from the group comprising: —H and C$_{1-4}$ alkyl, and R and R' join to form a 5 to 8 membered ring together with the atoms to which they are bonded;

each R"' is selected from the group comprising: H, C$_{1-4}$ alkyl, OR" and SR"; and each R"" is selected from the group comprising: H, OH and SH;

R$^{52}$ is selected from the group comprising: H, substituted or unsubstituted C$_{1-4}$alkyl and halogen;

R$^{53}$ is selected from the group comprising: —NR"C(=O)R" and —N=CR"(C$_{1-3}$alkyl);

R$^{54}$ is a substituted or unsubstituted C$_{1-6}$alkyl; provided that the compound is not

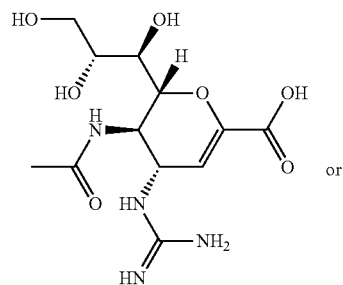

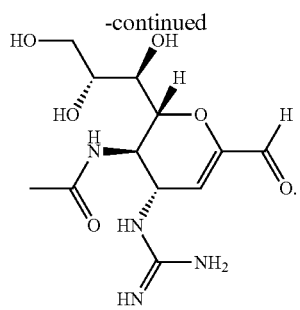

In an embodiment, when R$^{53}$ is —NHR(=O)Me, R$^{54}$ is not —COOH or —CHO.

In an embodiment, R$^{51}$ is —COOR". Preferably, R$^{51}$ is —COOH. In another embodiment, R$^{51}$ is —CR"O, preferably —CHO. In another embodiment, R$^{51}$ is —CR"'=NOR". Preferably, R"' is H. Preferably, R$^{51}$ is —CSR"=NOR". Preferably, R$^{51}$ is —COR"=NOR". Preferably, R" is H. Preferably, R$^{51}$ is —CR"=NOH, more preferably —CH=NOH. In another embodiment, R$^{51}$ is

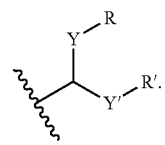

In an embodiment, R$^{52}$ is H.

In an embodiment, R$^{53}$ is —NR"C(=O)R", preferably —NHC(=O)Me. In another embodiment, R$^{53}$ is —N=CR"(C$_{1-3}$alkyl), preferably —N=CH(C$_{1-3}$alkyl). Preferably the C$_{1-3}$alkyl is methyl.

In an embodiment, R$^{54}$ is a C$_{1-6}$alkyl substituted with hydroxy. In an embodiment, R$^{54}$ is —CHY'R"—CHY'R"—CH$_2$Y'R" wherein each Y' is independently S or O and wherein each R" is independently —H, -Me, —Cl or —F. In an embodiment, R$^{54}$ is

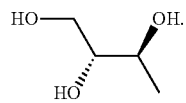

In an embodiment, Y, Y', R and R' are each as defined as in the embodiments of the second aspect for the compounds of formula I.

In an embodiment, the compound of formula VI is selected from the group comprising:

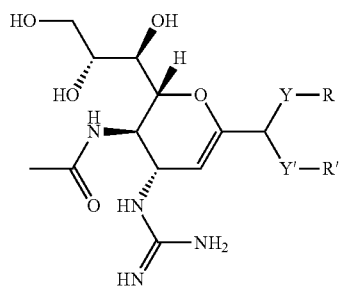

-continued
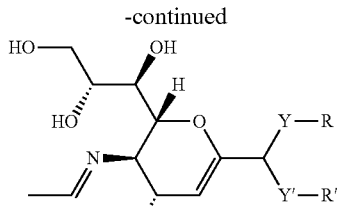
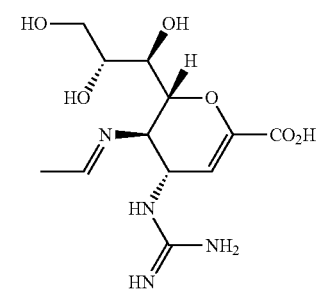
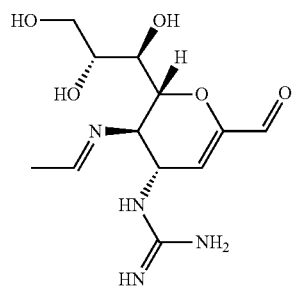
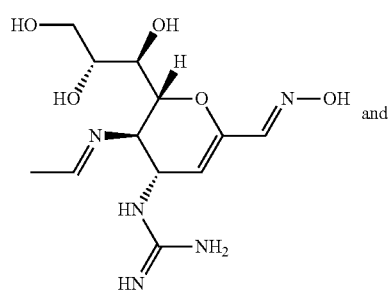
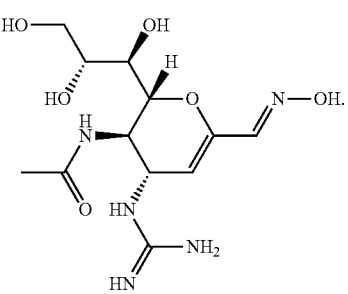
In an embodiment, the compound of formula VI is selected from the group comprising:
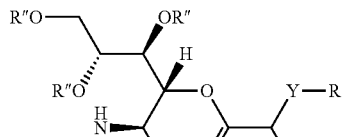
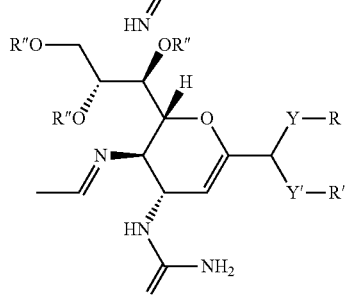
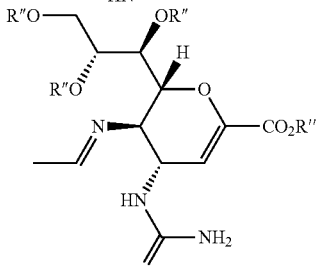
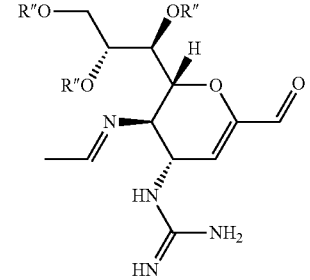
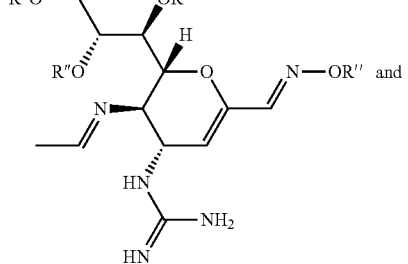 and
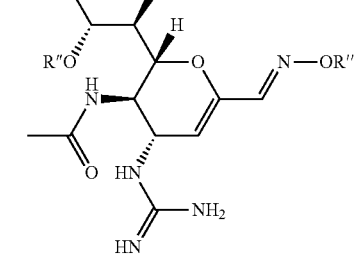

The present invention also includes the synthesis of all pharmaceutically acceptable isotopically-labelled compounds of formulae (I) to (VI) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection.

Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{15}$F, $^{15}$O and $^{13}$N, can be useful in Positron Emission Topography (PET) studies for examining substrate receptor occupancy.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention will now be illustrated by the following Examples which are intended to demonstrate specific embodiments of the invention but which are not to be construed as limiting.

The known active drug compounds, and their derivatives in unoxidised or reduced form, can be prepared by known methods described in the literature and patent literature relative to those compounds. The novel oxidised or reduced forms of the present invention may generally be prepared from the prior art compounds by conventional synthetic procedures for conducting oxidation and reduction reactions, using protecting or masking groups where necessary. Standard texts referring to such procedures are mentioned above. Examples of the synthetic routes for preparing a number of compounds according to the invention are illustrated below (for NMR, couplings constants are quoted in Hz).

EXAMPLE 1

Fluoroquinolone Derivatives

Formation of fluoroquinolone aldehyde derivatives have been undertaken by modifying a reduction/decarboxylation/Claisen addition/oxidation protocol reported by Kondo et al. (Kondo, H.; Sakamoto, F.; Kawakami, K.; Tsukamoto, G. *J. Med. Chem.*, 1988, 31, 221.)

Fluoroquinolone Aldehyde Synthesis

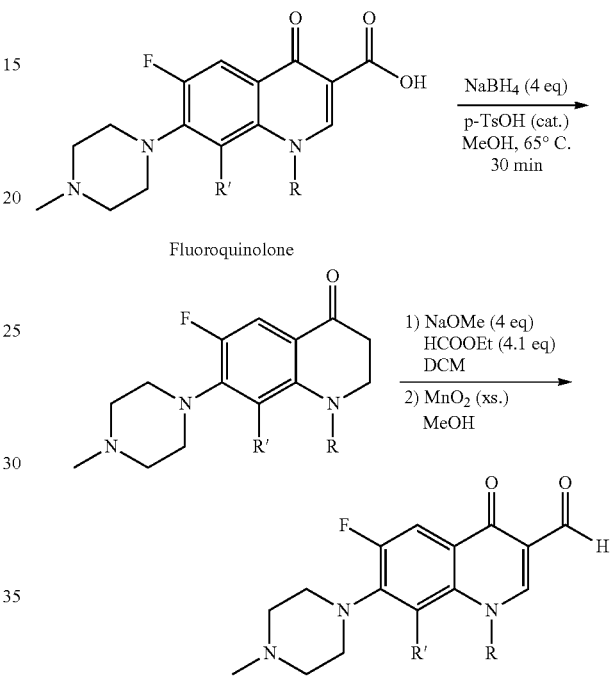

To a 0° C. stirring solution of fluoroquinolone in anhydrous methanol under inert atmosphere was added solid sodium borohydride (4.5 eq.) slowly over 30 minutes. The mixture was allowed to warm to room temperature and p-toluene sulfonic acid (0.1 eq.) was added. After heating at reflux for 3.5 hours, the mixture was allowed to cool and the solvent removed in vacuo. The crude solid was washed with hot chloroform and water and then extracted with chloroform (×3). The combined organic extracts were dried (magnesium sulfate), filtered and concentrated under reduced pressure. The crude mixture was subjected to flash column chromatography (20% methanol/chloroform) to afford the intermediate.

To a room temperature stirring solution of fluoroquinolone intermediate in anhydrous dichloromethane under inert atmosphere was added sodium methoxide (3.9 eq.) and ethyl formate (3.94 eq.). After eighteen hours, the mixture was quenched with ice-water. After separation, the organic layer was washed with 3 M sodium hydroxide (×2). The aqueous washings were acidified to pH 6 with concentrated hydrochloric acid and then extracted with dichloromethane (×3). The combined organic extracts were dried (magnesium sulfate), filtered and concentrated under reduced pressure. The crude mixture was dissolved in anhydrous methanol and manganese dioxide was added (excess). After stirring at room temperature for eighteen hours, the mixture washed filtered through Celite®. After flushing the filter cake with methanol and dichloromethane, the solvent was removed in vacuo and the crude solid subjected to flash column chromatography (20% methanol/chloroform) to afford the desired fluoroquinolone aldehyde.

Levofloxacin Aldehyde

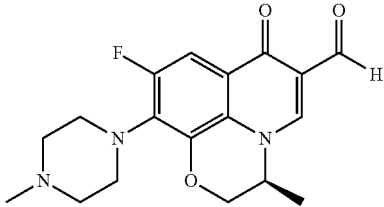 [SMILES: C[C@H]1COc2c(N3CCN(C)CC3)c(F)cc3c(=O)c(C=O)cn1c23]

Title compound was formed as a yellow solid in 46%.

$^1$H NMR, 400 MHz (CDCl$_3$) δ 10.39 (1H, s), 8.15 (1H, s), 7.75 (1H, d, J=12.4), 4.42-4.30 (3H, m), 3.36 (4H, m), 2.55 (4H, m), 2.37 (3H, s) and 1.59 (3H, d, J=7.2).

Pefloxacin Aldehyde

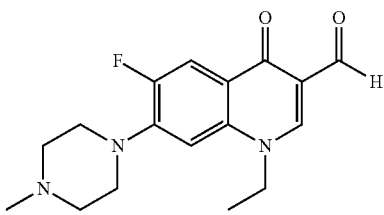 [SMILES: CCn1cc(C=O)c(=O)c2cc(F)c(N3CCN(C)CC3)cc21]

Title compound was formed as an off-white solid in 50%.

$^1$H NMR, 400 MHz (CDCl$_3$) δ 10.39 (1H, s), 8.25 (1H, s), 8.08 (1H, d, J=12.8), 6.78 (1H, d, J=6.8), 4.23 (2H, q, J=7.2), 3.30 (4H, t, J=4.8), 2.64 (4H, t, J=4.8), 2.39 (3H, s) and 1.56 (3H, t, J=7.6).

Procedure for Oxime Formation

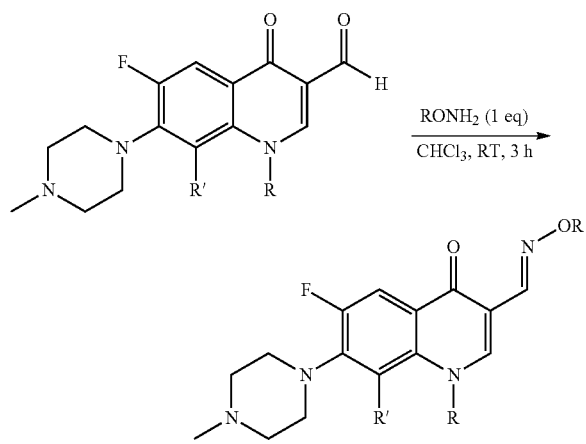

To a room temperature stirring solution of fluoroquinolone aldehyde in anhydrous chloroform under inert atmosphere was added o-substituted hydroxylamine (1 eq.). After three hours, the mixture was partitioned between chloroform/water and extracted with chloroform (×2). The combined organic extracts were dried (magnesium sulfate), filtered and concentrated under reduced pressure. The crude mixture was subjected to flash column chromatography (5% methanol/chloroform) to afford the product as an off-white solid.

Procedure for Oxime Formation (from o-Substituted Hydroxylamine Hydrochloride Salt)

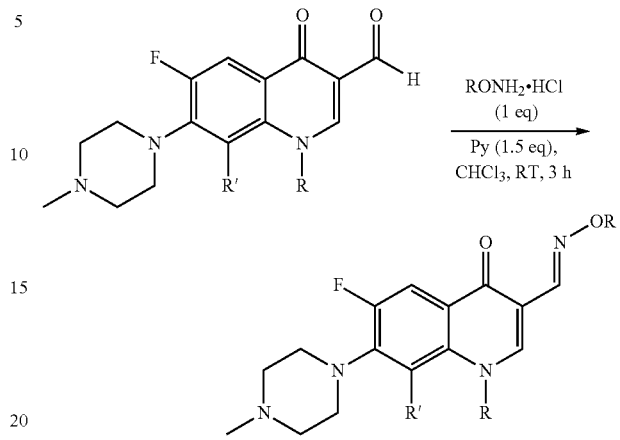

To a room temperature stirring solution of fluoroquinolone aldehyde in anhydrous chloroform under inert atmosphere was added o-substituted hydroxylamine hydrochloride salt (1 eq.), followed by anhydrous pyridine (1.5 eq.). After three hours, the mixture was partitioned between chloroform/water and extracted with chloroform (×2). The combined organic extracts were dried (magnesium sulfate), filtered and concentrated under reduced pressure. The crude mixture was subjected to flash column chromatography (5% methanol/chloroform) to afford the product as an off-white solid.

Levofloxacin Aldehyde Benzyl Oxime

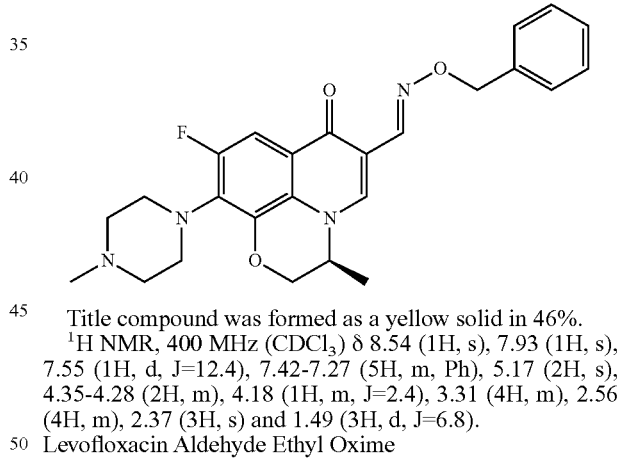

Title compound was formed as a yellow solid in 46%.

$^1$H NMR, 400 MHz (CDCl$_3$) δ 8.54 (1H, s), 7.93 (1H, s), 7.55 (1H, d, J=12.4), 7.42-7.27 (5H, m, Ph), 5.17 (2H, s), 4.35-4.28 (2H, m), 4.18 (1H, m, J=2.4), 3.31 (4H, m), 2.56 (4H, m), 2.37 (3H, s) and 1.49 (3H, d, J=6.8).

Levofloxacin Aldehyde Ethyl Oxime

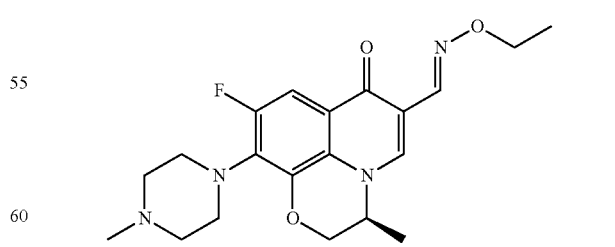

Title compound was formed as a yellow solid in 36%.

$^1$H NMR, 400 MHz (CDCl$_3$) δ 8.46 (1H, s), 8.00 (1H, s), 7.60 (1H, d, J=12.4), 4.40-4.23 (3H, m), 4.17 (2H, q, J=6.8), 3.39-3.31 (4H, m), 2.56 (4H, m), 2.37 (3H, s), 1.55 (3H, d, J=6.8) and 1.36 (3H, t, J=6.8).

Levofloxacin Aldehyde Trityl Oxime

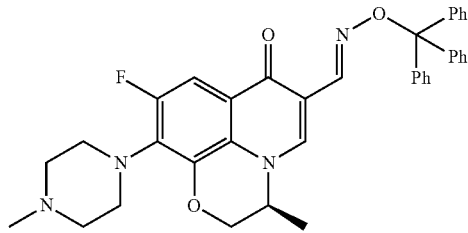 [SMILES: C[C@H]1COc2c(N3CCN(C)CC3)c(F)cc3c(=O)c(/C=N/OC(c4ccccc4)(c4ccccc4)c4ccccc4)cn1c23]

Title compound was formed as a yellow solid in 57%.
¹H NMR, 400 MHz (CDCl₃) δ 8.59 (1H, s), 7.47 (1H, d, J=12.4), 7.36 (1H, s), 7.36-7.14 (15H, m, 3×Ph), 4.14 (2H, m), 3.82 (1H, m), 3.26 (4H, t, J=4.4), 2.47 (4H, t, J=4.4), 2.29 (3H, s) and 1.27 (3H, d, J=6.8).

Levofloxacin Aldehyde Pentafluorobenzyl Oxime

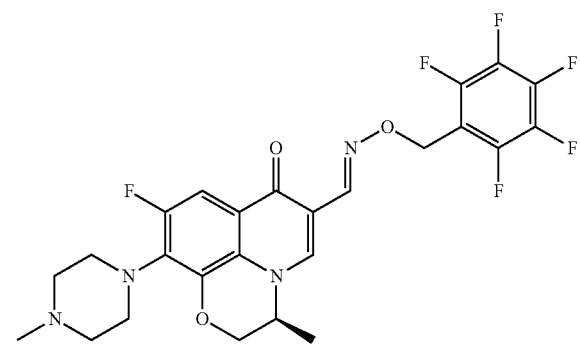 [SMILES: C[C@H]1COc2c(N3CCN(C)CC3)c(F)cc3c(=O)c(/C=N/OCc4c(F)c(F)c(F)c(F)c4F)cn1c23]

Title compound was formed as a yellow solid in 58%.
¹H NMR, 400 MHz (CDCl₃) δ 8.44 (1H, s), 7.96 (1H, s), 7.57 (1H, d, J=12.4), 5.20 (2H, s), 4.35-4.28 (2H, m), 4.18 (1H, m, J=2.4), 3.31 (4H, m), 2.56 (4H, m), 2.37 (3H, s) and 1.49 (3H, d, J=6.8).

Levofloxacin Aldehyde para-Nitrobenzyl Oxime

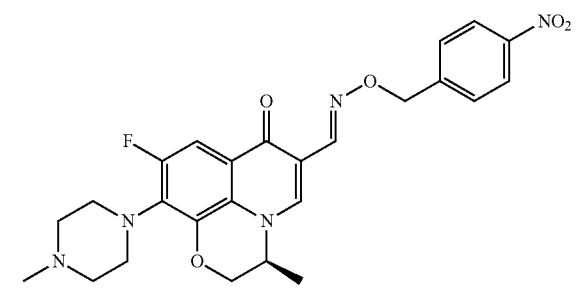 [SMILES: C[C@H]1COc2c(N3CCN(C)CC3)c(F)cc3c(=O)c(/C=N/OCc4ccc([N+](=O)[O-])cc4)cn1c23]

Title compound was formed in 52%.
¹H NMR, 400 MHz (CDCl₃) δ 8.59 (1H, s), 8.20 (2H, d, J=8.7), 7.96 (1H, s), 7.62 (1H, d, J=12.4), 7.53 (2H, d, J=8.7), 5.20 (2H, s), 4.40-4.29 (3H, m), 3.40-3.30 (4H, m), 2.58-2.54 (4H, m), 2.37 (3H, s) and 1.56 (3H, d, J=7.2).

Levofloxacin Aldehyde tert-Butyl Oxime

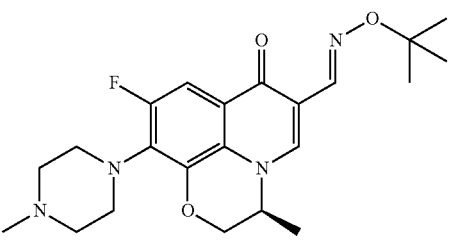 [SMILES: C[C@H]1COc2c(N3CCN(C)CC3)c(F)cc3c(=O)c(/C=N/OC(C)(C)C)cn1c23]

Title compound was formed in 100%.
¹H NMR, 400 MHz (CDCl₃) δ 8.46 (1H, s), 8.02 (1H, s), 7.69 (1H, d, J=12.4), 4.38-4.29 (3H, m), 3.45 (4H, m), 2.75 (4H, m), 2.50 (3H, s), 1.57 (3H, d, J=6.8) and 1.34 (9H, s).

Pefloxacin Aldehyde Benzyl Oxime

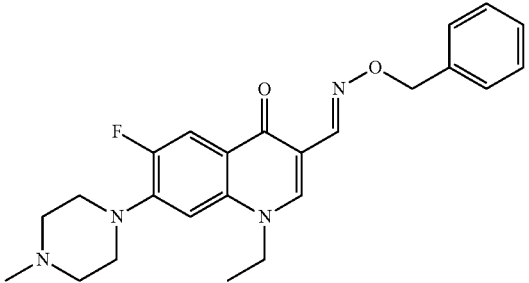 [SMILES: CCn1cc(/C=N/OCc2ccccc2)c(=O)c2cc(F)c(N3CCN(C)CC3)cc21]

Title compound was formed as a white solid in 47%.
¹H NMR, 400 MHz (CDCl₃) δ 8.57 (1H, s), 8.07 (1H, s), 7.98 (1H, d, J=13.2), 7.42-7.27 (5H, m, Ph), 6.69 (1H, d, J=7.2), 5.17 (2H, s), 4.12 (2H, q, J=7.2), 3.26 (4H, t, J=4.8), 2.63 (4H, t, J=4.8), 2.38 (3H, s) and 1.48 (3H, d, J=7.2).

Acetal Formations

Levofloxacin Aldehyde Dimethoxy Acetal

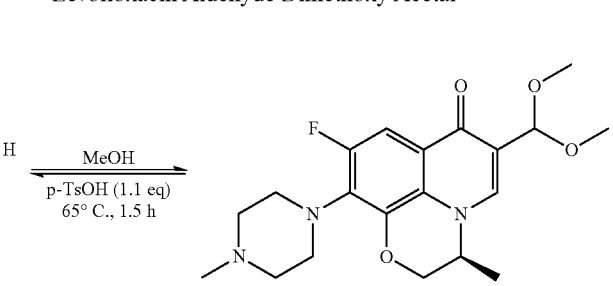

To a room temperature stirring solution of levofloxacin aldehyde (0.100 g, 0.26 mmol) in anhydrous methanol (20 mL) under inert atmosphere was added p-toluene sulfonic acid (0.050 g, 1.1 eq.). The mixture was heated at reflux for 1.5 hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure to afford the product as a white solid (94%).

$^1$H NMR, 400 MHz (CDCl$_3$) δ 7.69 (1H, s), 7.68 (1H, d, J=12.8), 5.68 (1H, s), 4.34 (1H, m), 4.27-4.23 (2H, m), 3.47 (6H, s), 3.35 (4H, m), 2.55 (4H, m), 2.36 (3H, s) and 1.52 (3H, d, J=7.2).

Levofloxacin Aldehyde Diethoxy Acetal

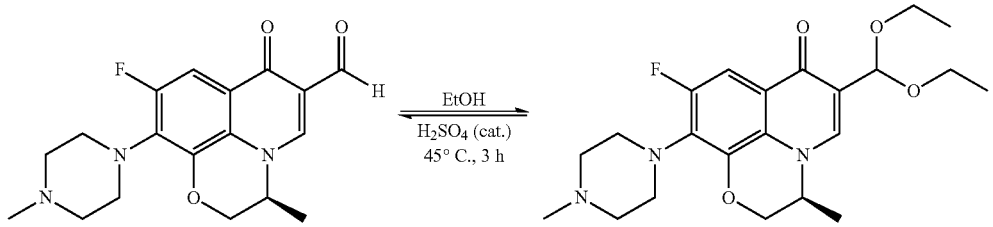 [SMILES: "EtOH" ; C[C@H]1COc2c(N3CCN(C)CC3)c(F)cc3c(=O)c(C=O)cn1c23 ; CCOC(OCC)c1cn2c3c(c(N4CCN(C)CC4)c(F)cc3c1=O)OC[C@@H]2C]

To a room temperature stirring solution of levofloxacin aldehyde dimethoxy acetal (0.100 g, 0.24 mmol) in anhydrous ethanol (20 mL) under inert atmosphere was added 4 Å molecular sieves and 6 drops of concentrated sulfuric acid. The mixture was heated at 45° C. for three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (10% methanol/dichloromethane) to afford the product as a yellow oil in quantitative yield.

$^1$H NMR, 400 MHz (CDCl$_3$) δ 7.76 (1H, s), 7.67 (1H, d, J=12.8), 5.81 (1H, s), 4.36 (1H, m), 4.25-4.22 (2H, m), 3.84-3.76 (2H, m), 3.69-3.63 (2H, m), 3.34 (4H, m), 2.55 (4H, m), 2.36 (3H, s), 1.52 (3H, d, J=6.8), 1.254 (3H, t, J=7.2) and 1.252 (3H, t, J=7.2).

Levofloxacin Aldehyde Di-n-propoxy Acetal

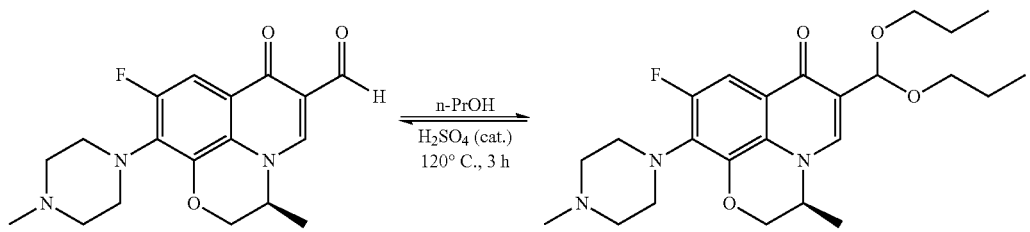

To a room temperature stirring solution of levofloxacin aldehyde (0.100 g, 0.22 mmol) in anhydrous n-propanol (20 mL) under inert atmosphere was added 4 Å molecular sieves and 3 drops of concentrated sulfuric acid. The mixture was heated at 120° C. for three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (10% methanol/dichloromethane) to afford the product as a yellow oil (57%).

$^1$H NMR, 400 MHz (CDCl$_3$) δ 7.75 (1H, s), 7.67 (1H, d, J=12.4), 5.79 (1H, s), 4.35 (1H, m), 4.27-4.24 (2H, m), 3.71-3.67 (2H, m), 3.56-3.51 (2H, m), 3.38 (4H, m), 2.60 (4H, m), 2.39 (3H, s), 1.68-1.62 (4H, m), 1.52 (3H, d, J=7.2) and 0.95 (6H, t, J=7.2).

Levofloxacin Aldehyde Dioxolano Acetal

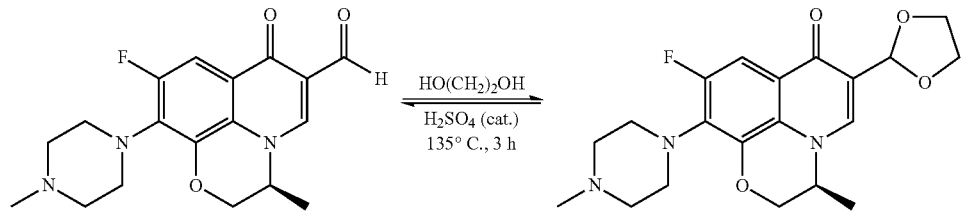

To a room temperature stirring solution of levofloxacin aldehyde (0.100 g, 0.22 mmol) in anhydrous ethylene glycol (20 mL) under inert atmosphere was added 4 Å molecular sieves and 6 drops of concentrated sulfuric acid. The mixture was heated at 135° C. for three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (15% methanol/dichloromethane) to afford the product as a yellow oil (30%).

$^1$H NMR, 400 MHz (CDCl$_3$) δ 7.72 (1H, s), 7.62 (1H, d, J=12.4), 6.08 (1H, s), 4.39 (1H, m), 4.36-4.29 (2H, m), 4.15 (2H, m), 4.06 (2H, m), 3.36 (4H, m), 2.60 (4H, m), 2.40 (3H, s) and 1.51 (3H, d, J=7.2).

EXAMPLE 2

Pregabalin Derivatives

Pregabalin Phthalic Imide

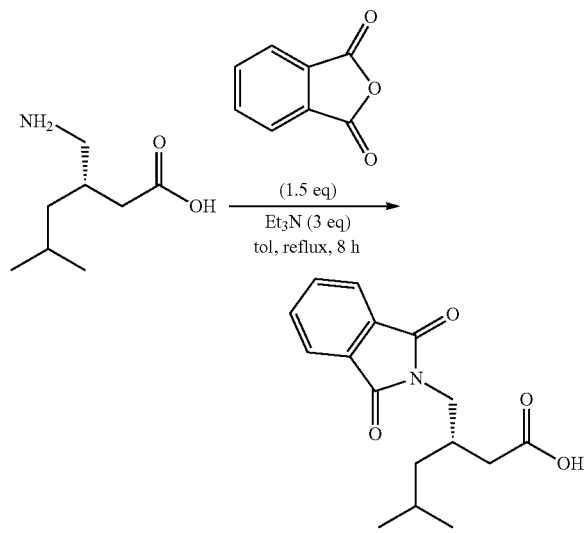

To a room temperature stirring solution of pregabalin (1.5 g, 9.43 mmol) in anhydrous toluene (45 mL) under inert atmosphere was added triethylamine (3.9 mL, 3 eq.) and phthalic anhydride (2.0 g, 1.5 eq.). The mixture was heated at reflux for eight hours. After allowing the mixture to cool to 0° C., the mixture was acidified to pH 2 and extracted with ethyl acetate (×3). The combined organic extracts were dried (magnesium sulfate), filtered and concentrated under reduced pressure. The crude mixture was subjected to flash column chromatography (40% ethyl acetate/hexane) to afford the product as a white solid (2.4 g, 88%).

$^1$H NMR, 400 MHz (CDCl$_3$) δ 7.83 (2H, d, J=8.0), 7.72 (2H, d, J=8.0), 3.71 (1H, dd, J=14.0, 4.0), 3.62 (1H, dd, J=14.0, 8.0), 2.44-2.24 (3H, m), 1.75 (1H, sep, J=6.8), 1.23 (2H, m), 0.95 (3H, d, J=6.4) and 0.90 (3H, d, J=6.4).

Pregabalin Phthalimidine Alcohol

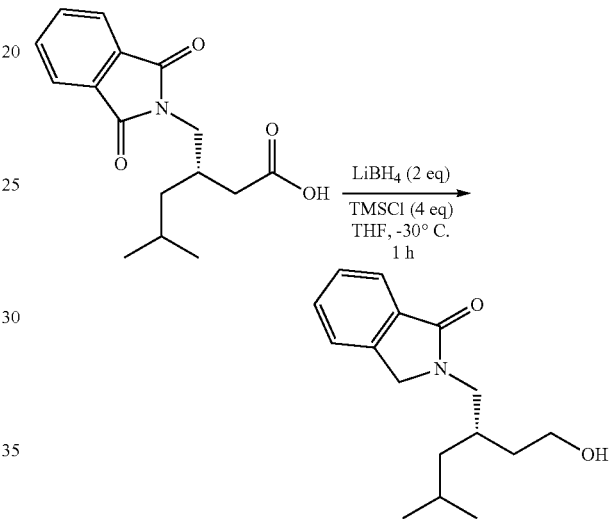

To a −30° C. stirring solution of pregabalin phthalic imide (2.4 g, 8.30 mmol) in anhydrous tetrahydrofuran (80 mL) under inert atmosphere was added lithium borohydride (8.3 mL, 2.0 eq.). After one hour, the mixture was allowed to warm to 0° C., quenched with aqueous ammonium chloride solution and extracted with dichloromethane (×3). The combined organic extracts were dried (magnesium sulfate), filtered and concentrated under reduced pressure. The crude mixture was subjected to flash column chromatography (50% ethyl acetate/hexane) to afford the product as a white solid (1.2 g, 54%).

$^1$H NMR, 400 MHz (CDCl$_3$) δ 7.84 (1H, d, J=7.6), 7.54-7.44 (3H, m), 4.48 (1H, d, J=16.8), 4.38 (1H, d, J=17.2), 3.76 (2H, m), 3.46 (1H, m), 2.60 (1H, br s), 1.71 (2H, m), 1.59 (2H, m), 1.26 (2H, m), 0.95 (3H, d, J=6.8) and 0.90 (3H, d, J=6.8).

Pregabalin Phthalimidine Aldehyde

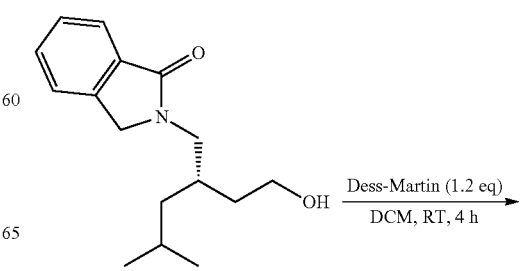

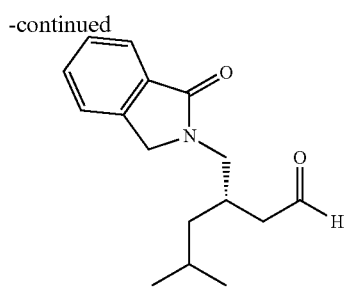

To a room temperature stirring solution of pregabalin phthalic imide (0.58 g, 2.11 mmol) in anhydrous dichloromethane (50 mL) under inert atmosphere was added Dess-Martin periodinane (1.07 g, 1.2 eq.). After four hours, the mixture was partitioned between diethyl ether (50 mL) and 1 M sodium hydroxide solution (50 mL). The organic phase was dried (magnesium sulfate), filtered and concentrated under reduced pressure. The crude mixture was subjected to flash column chromatography (50% ethyl acetate/hexane) to afford the product as a yellow oil (1.2 g, 54%).

$^1$H NMR, 400 MHz (CDCl$_3$) δ 9.73 (1H, s, CHO), 7.83 (1H, d, J=7.6), 7.56-7.44 (3H, m), 4.45 (1H, d, J=16.8), 4.33 (1H, d, J=17.2), 3.62 (1H, dd, J=14.0, 8.4), 3.45 (1H, dd, J=14.0, 5.2), 2.59-2.53 (2H, m), 2.43 (1H, m), 1.66 (1H, sep, J=6.4), 1.26 (2H, m), 0.95 (3H, d, J=6.8) and 0.90 (3H, d, J=6.4).

Pregabalin Phthalimidine Aldehyde Benzyl Oxime

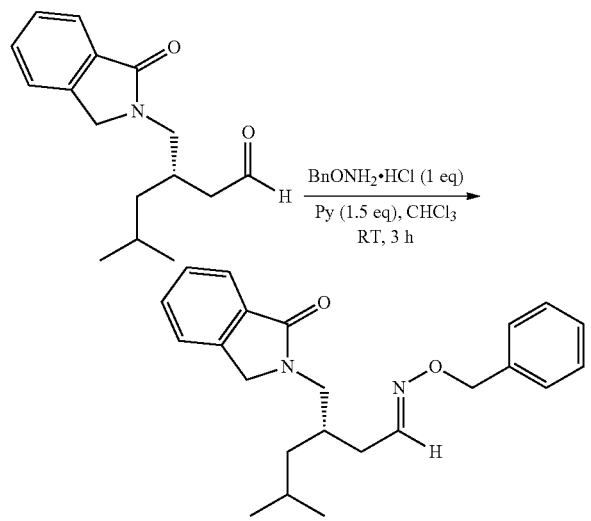

To a room temperature stirring solution of pregabalin phthalic imide aldehyde (0.103 g, 0.38 mmol) in anhydrous chloroform (5 mL) under inert atmosphere was added o-benzylhydroxylamine hydrochloride salt (0.060 g, 1 eq.), followed by anhydrous pyridine (0.05 mL, 1.5 eq.). After three hours, the mixture was partitioned between chloroform/water and extracted with chloroform (×2). The combined organic extracts were dried (magnesium sulfate), filtered and concentrated under reduced pressure. The crude mixture was subjected to flash column chromatography (5% methanol/chloroform) to afford the product as a yellow oil (49%).

$^1$H NMR, 400 MHz (CDCl$_3$) δ 7.83 (2H, d, J=11.6), 7.52-7.45 (3H, m), 7.36-7.25 (5H, m), 6.76 (1H, t, J=5.6), 5.06 (2H, s) 5.00 (s, minor isomer), 4.33-4.24 (2H, m), 3.53-3.47 (2H, m), 2.35 (1H, m), 2.21 (1H, m), 1.70 (1H, m), 1.28-1.19 (2H, m), 0.90 (3H, d, J=6.4) and 0.87 (3H, d, J=6.8).

Pregabalin Phthalimidine Aldehyde Dimethoxy Acetal

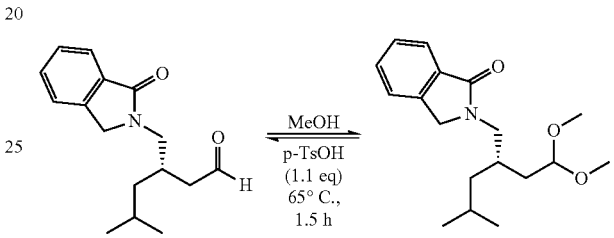

To a room temperature stirring solution of pregabalin phthalic imide aldehyde (0.101 g, 0.37 mmol) in anhydrous methanol (20 mL) under inert atmosphere was added p-toluene sulfonic acid (0.070 g, 1.1 eq.). The mixture was heated at 40° C. for two hours, followed by heating at reflux for a further three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (1/3 ethyl acetate/hexane) to afford the product as a yellow oil (63%).

$^1$H NMR, 400 MHz (CDCl$_3$) δ 7.85 (1H, d, J=7.6), 7.55-7.43 (3H, m), 4.47 (1H, t, J=5.6), 4.42 (1H, d, J=16.8), 4.39 (1H, d, J=16.8), 3.58 (1H, dd, J=14.0, 7.6), 3.51 (1H, dd, J=14.0, 6.8), 3.29 (3H, s), 3.27 (3H, s), 2.02 (1H, m), 1.72 (1H, m), 1.68-1.59 (2H, m), 1.27-1.17 (2H, m), 0.91 (3H, d, J=6.4) and 0.88 (3H, d, J=6.4).

Pregabalin Phthalimidine Aldehyde Dioxolano Acetal

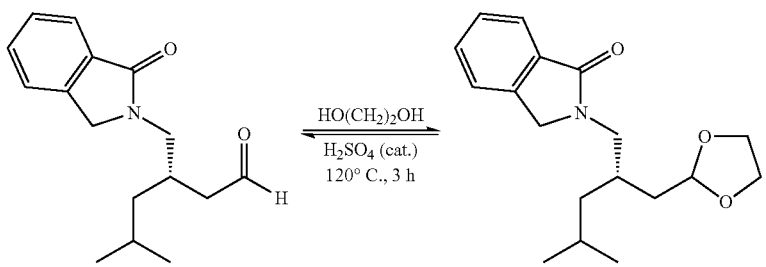

To a room temperature stirring solution of pregabalin phthalic imide aldehyde (0.987 g, 0.36 mmol) in anhydrous ethylene glycol (20 mL) under inert atmosphere was added 6 drops of concentrated sulfuric acid. The mixture was heated at 120° C. for three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (1/3 ethyl acetate/hexane) to afford the product as a yellow oil (62%).

$^1$H NMR, 400 MHz (CDCl$_3$) δ 7.85 (1H, d, J=7.2), 7.53-7.43 (3H, m), 4.94 (1H, t, J=4.8), 4.44 (1H, d, J=16.8), 4.36 (1H, d, J=16.8), 3.92 (2H, m), 3.81 (2H, m), 3.62 (1H, dd, J=14.0, 6.4), 3.55 (1H, dd, J=13.6, 6.8), 2.11 (1H, m), 1.73-1.65 (3H, m), 1.31-1.20 (2H, m), 0.91 (3H, d, J=6.8) and 0.87 (3H, d, J=6.4).

Supplementary Information

Phthalimidine protecting group may be removed by oxidizing to the corresponding phthalimide using 2,2'-bipyridinium chlorochromate (2 eq.) and meta-chloroperoxybenzoic acid (5 eq.) in the presence of Celite® with dichloromethane as the solvent (Luzzio, F. A.; Zacherl, D. P.; Figg, W. D. *Tetrahedron Lett.*, 1999, 11, 2087). Following this, the phthalimido group may be removed by reacting the compound with hydrazine in refluxing methanol (Lagu, B.; Tian, D.; Jeon, Y.; Li, C.; Wetzel, J. M.; Nagarathnam, D.; Shen, Q.; Forray, C.; Chang, R. S. L.; Broten, T. P.; Ransom, R. W.; Chan, T-B.; O'Malley, S. S.; Schorn, T. W.; Rodrigues, A. D.; Kassahun, K.; Pettibone, D. J.; Freidinger, R.; Gluchowski, C. *J. Med. Chem.*, 2000, 43, 2775).

EXAMPLE 3

Oseltamivir Derivatives

Oseltamivir Boc-Amide

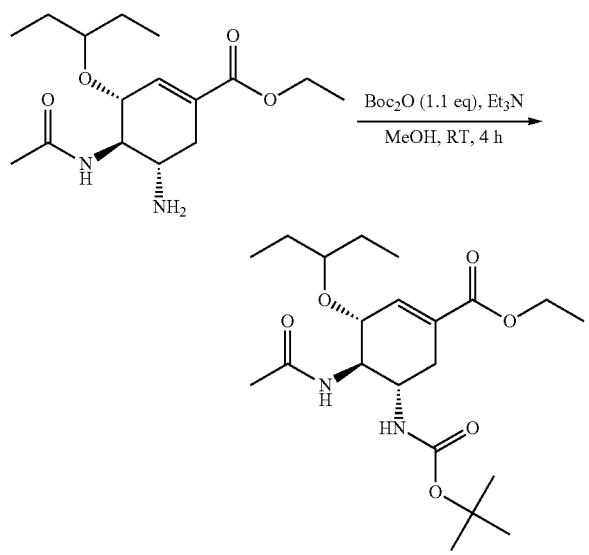

To a room temperature stirring solution of oseltamivir (1.5 g, 4.81 mmol) in anhydrous methanol (50 mL) under inert atmosphere was added di-tert-butyl dicarbonate (1.15 g, 1.1 eq.) and triethylamine (2 mL). After four hours, the crude mixture was concentrated under reduced pressure and subjected to flash column chromatography (30% methanol/dichloromethane) to afford the product as a white solid (1.6 g, 90%).

$^1$H NMR, 400 MHz (CDCl$_3$) δ 6.80 (1H, s), 5.72 (1H, d, J=9.2), 5.07 (1H, d, J=9.1), 4.21 (2H, dq, J=6.7, 1.7), 4.08 (1H, q, J=9.1), 3.95 (1H, m), 3.80 (1H, m), 3.35 (1H, m), 2.74 (1H, dd, J=17.8, 5.1), 2.29 (1H, m), 1.99 (3H, s), 1.51 (4H, m), 1.42 (9H, s), 1.29 (3H, t, J=7.2) and 0.89 (6H, d, J=7.4).

Oseltamivir Boc-Amide Alcohol

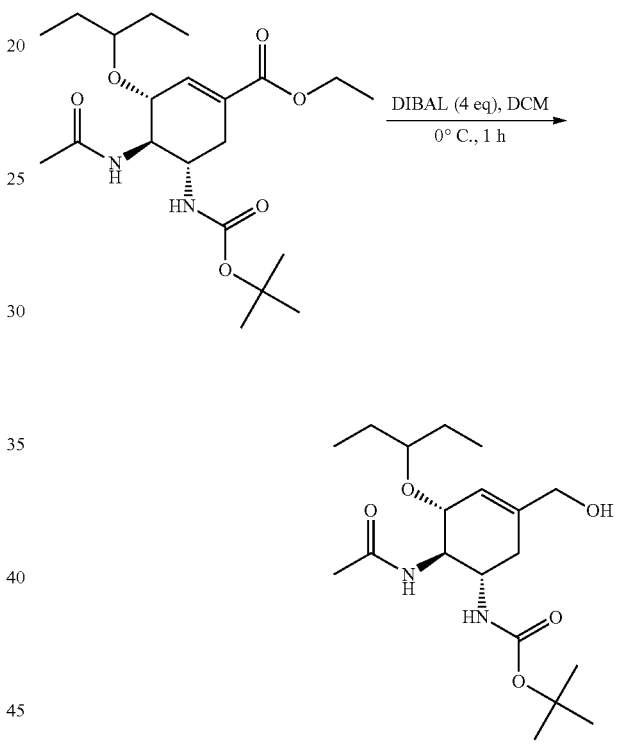

To a 0° C. stirring solution of oseltamivir Boc-amide (1.33 g, 3.23 mmol) in anhydrous dichloromethane (100 mL) under inert atmosphere was added di-iso-butyl aluminium hydride (12.92 mL, 1.2 eq.). After one hour, the mixture was partitioned between dichloromethane (50 mL) and 1 M sodium hydroxide solution (50 mL). The organic phase was dried (magnesium sulfate), filtered and concentrated under reduced pressure. The crude mixture was subjected to flash column chromatography (5% methanol/dichloromethane) to afford the product (0.34 g, 34%).

$^1$H NMR, 400 MHz (CDCl$_3$) δ 6.22 (1H, d, J=9.2), 5.66 (1H, s), 5.33 (1H, d, J=9.3), 4.09-4.05 (2H, m), 3.91 (1H, m), 3.88 (1H, m), 3.33 (1H, quin, J=5.6), 2.53 (1H, br s), 2.34 (1H, dd, J=7.2, 5.1), 2.11 (1H, m), 1.99 (3H, s), 1.52-1.45 (4H, m), 1.42 (9H, s) and 0.90-0.85 (6H, m).

Oseltamivir Boc-Amide Aldehyde

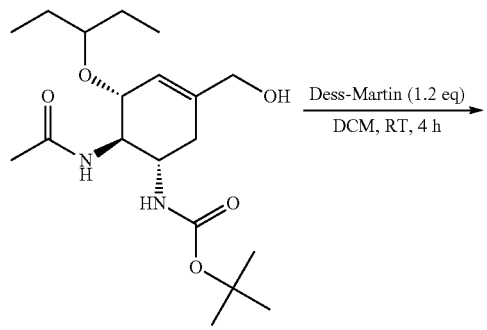
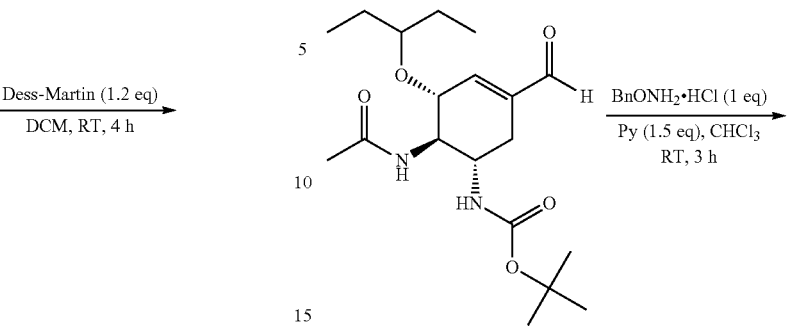

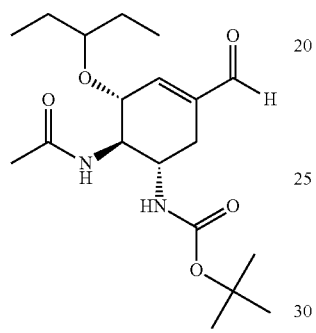
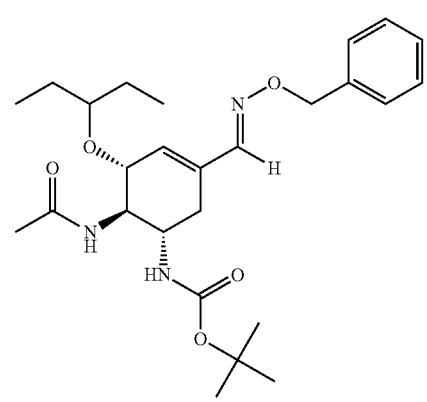

To a room temperature stirring solution of oseltamivir Boc-amide alcohol (1.57 g, 4.24 mmol) in anhydrous dichloromethane (150 mL) under inert atmosphere was added Dess-Martin periodinane (2.15 g, 1.2 eq.). After four hours, the mixture was partitioned between dichloromethane (50 mL) and 1 M sodium hydroxide solution (50 mL). The organic phase was dried (magnesium sulfate), filtered and concentrated under reduced pressure. The crude mixture was subjected to flash column chromatography (5% methanol/dichloromethane) to afford the product as yellow oil (1.2 g, 54%).

$^1$H NMR, 400 MHz (CDCl$_3$) δ 9.50 (1H, s), 6.61 (1H, s), 5.83 (1H, d, J=8.7), 4.96 (1H, d, J=9.1), 4.16-4.07 (2H, m), 3.80 (1H, m), 3.38 (1H, quin, J=5.6), 2.74 (1H, dd, J=17.9, 5.2), 2.13 (1H, m), 2.00 (3H, s), 1.58-1.48 (4H, m), 1.43 (9H, s), 0.95-0.87 (6H, m).

Oseltamivir Boc-Amide Aldehyde Benzyl Oxime

To a room temperature stirring solution of oseltamivir Boc-amide aldehyde (0.153 g, 0.41 mmol) in anhydrous chloroform (5 mL) under inert atmosphere was added o-benzylhydroxylamine hydrochloride salt (0.067 g, 1 eq.), followed by anhydrous pyridine (0.051 mL, 1.5 eq.). After three hours, the mixture was partitioned between chloroform/water and extracted with chloroform (×2). The combined organic extracts were dried (magnesium sulfate), filtered and concentrated under reduced pressure. The crude mixture was subjected to flash column chromatography (5% methanol/chloroform) to afford the product as an off-white foam (69%).

$^1$H NMR, 400 MHz (CDCl$_3$) δ 7.68 (1H, s), 7.37-7.30 (5H, m), 6.02 (1H, d, J=9.2), 5.80 (1H, s), 5.13 (1H, d, J=9.2), 5.09 (2H, s), 4.07 (1H, m), 3.96 (1H, m), 3.80 (1H, m), 3.31 (1H, quin, J=5.6), 2.75 (1H, dd), 2.25 (1H, m), 1.98 (3H, s), 1.52-1.46 (4H, m), 1.45 (9H, s), 0.89-0.85 (6H, m).

Oseltamivir Aldehyde Dioxolano Acetal (NB. Conditions have Also Removed the Boc Protecting Group)

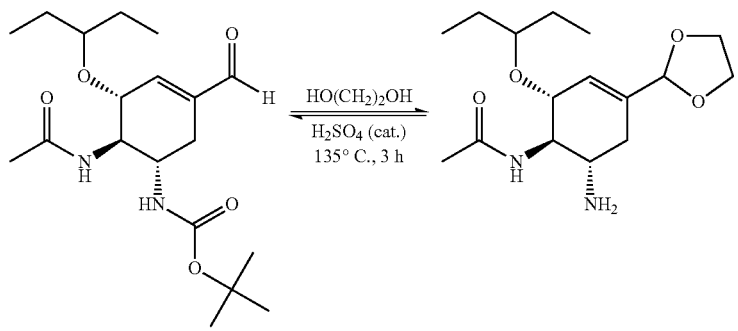

To a room temperature stirring solution of oseltamivir Boc-amide aldehyde (0.2 g, 0.54 mmol) in anhydrous ethylene glycol (30 mL) under inert atmosphere was added 6 drops of concentrated sulfuric acid. The mixture was heated at 135° C. for three hours. After allowing the mixture to cool to room temperature, the mixture was quenched with saturated sodium hydrogen carbonate solution (20 mL) and extracted with dichloromethane (3×20 mL). The combined organic extracts were dried (magnesium sulfate), filtered and concentrated under reduced pressure. The crude mixture was subjected to flash column chromatography (5% methanol/chloroform) to afford the product as a yellow oil.

$^1$H NMR, 400 MHz (CDCl$_3$) δ 6.38 (1H, m), 5.91 (1H, s), 5.16 (1H, s), 4.08 (1H, m), 3.98-3.96 (2H, m), 3.92-3.90 (2H, m), 3.36 (1H, quin), 2.92 (1H, m), 2.55 (1H, m), 2.05-1.97 (5H, m), 1.99 (3H, s), 1.56-1.49 (4H, m), 0.95-0.87 (6H, m).

The invention claimed is:

1. A compound of formula (III):

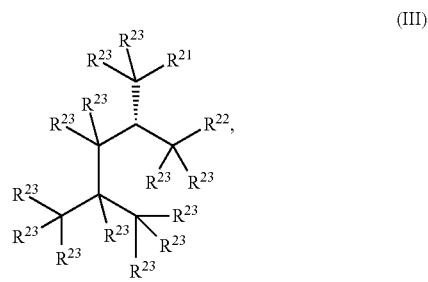

(III)

wherein:
each $R^{23}$ is independently selected from the group consisting of: —H, —F and $C_{1-3}$ alkyl;
$R^{21}$ is selected from the group consisting of: —NRR',

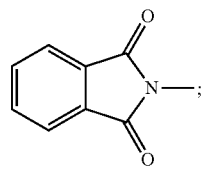

and
$R^{22}$ is selected from the group consisting of: —CHO, —CH=NOR''' and

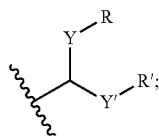

wherein:
—Y— is selected from the group consisting of: =N—, —O— and —S—;
—Y'— is selected from the group consisting of: —O— and —S—;
(i) each R and R' is independently selected from the group consisting of: —H and $C_{1-4}$ alkyl; or (ii) —NRR' represents a ring independently selected from the group consisting of: pyrrole, pyrroline, pyrrolidine, piperazine, piperidine, morpholine, azepane, azepine, diazepine, thiazepine and azocane, or (iii)

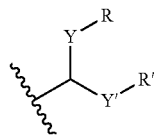

represents a ring independently selected from the group consisting of: dioxolane, dioxane, dithiolane and dithiane; and R''' is selected from the group consisting of: H, $C_{1-4}$ alkyl and —(CR''''R'''')$_n$-aryl; wherein R'''' is selected from the group consisting of: H and aryl and wherein n is from 1 to 4.

2. The compound of claim 1, wherein $R^{21}$ is —NH$_2$ and each $R^{23}$ is H.

3. The compound of claim 1, wherein $R^{22}$ is —CHO, —CH=NOH or

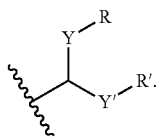

4. The compound of claim 2, wherein $R^{22}$ is —CHO, —CH=NOH or

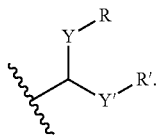

5. A compound of formula (III):

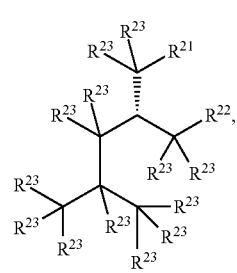

(III)

wherein the compound is

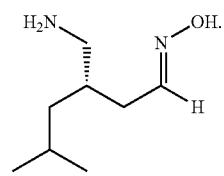

* * * * *

UNITED STATES PATENT AND TRADEMARK OFFICE
CERTIFICATE OF CORRECTION

PATENT NO. : 8,877,945 B2  Page 1 of 1
APPLICATION NO. : 13/319377
DATED : November 4, 2014
INVENTOR(S) : Derek Lindsay et al.

It is certified that error appears in the above-identified patent and that said Letters Patent is hereby corrected as shown below:

In the Claims

At column 51, claim number 1, line number 35, "–H, –F and $C_{1-3}$ alkyl" should read -- –H, –Cl, –F and $C_{1-3}$ alkyl;--

At column 51, claim number 1, line number 36, "$R^{21}$ is selected from the group consisting of:

–NRR', 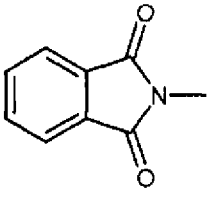 ; and" should read --$R^{21}$ is selected from the group consisting of: –NRR', 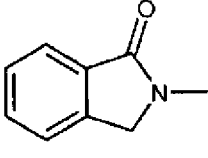 and 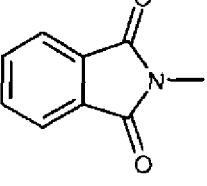 ; and--

Signed and Sealed this
Twenty-eighth Day of April, 2015

Michelle K. Lee
*Director of the United States Patent and Trademark Office*